(12) United States Patent
Newton et al.

(10) Patent No.: US 11,058,686 B2
(45) Date of Patent: Jul. 13, 2021

(54) 5-(PYRIMIDIN-4-YL)-2-(PYRROLIDIN-1-YL)-NICOTINONITRILE COMPOUNDS AS IKKE, TBK1 AND/OR SIK2 KINASES INHIBITORS

(71) Applicant: DOMAINEX LIMITED, Saffron Walden (GB)

(72) Inventors: Gary Karl Newton, Saffron Walden (GB); Mark Richard Stewart, Saffron Walden (GB)

(73) Assignee: DOMAINEX LIMITED, Saffron Walden (GB)

( * ) Notice: Subject to any disclaimer, the term of this patent is extended or adjusted under 35 U.S.C. 154(b) by 0 days.

(21) Appl. No.: 16/487,977

(22) PCT Filed: Feb. 23, 2018

(86) PCT No.: PCT/GB2018/050475
§ 371 (c)(1),
(2) Date: Aug. 22, 2019

(87) PCT Pub. No.: WO2018/154315
PCT Pub. Date: Aug. 30, 2018

(65) Prior Publication Data
US 2020/0030326 A1    Jan. 30, 2020

(30) Foreign Application Priority Data

Feb. 23, 2017   (GB) ...................... 1702947

(51) Int. Cl.
*A61K 31/506*    (2006.01)
*C07D 401/14*    (2006.01)

(52) U.S. Cl.
CPC .......... *A61K 31/506* (2013.01); *C07D 401/14* (2013.01)

(58) Field of Classification Search
CPC combination set(s) only.
See application file for complete search history.

(56) References Cited

U.S. PATENT DOCUMENTS

| | | |
|---|---|---|
| 8,969,335 B2 | 3/2015 | Hoelzemann et al. |
| 8,981,101 B2 | 3/2015 | Dorsch et al. |
| 9,079,910 B2 | 7/2015 | Dorsch et al. |
| 9,102,675 B2 | 8/2015 | Dorsch et al. |
| 2013/0267491 A1* | 10/2013 | Perrior ............... A61P 31/04 514/210.2 |
| 2016/0000784 A1* | 1/2016 | Newton ............... A61P 29/00 514/210.2 |

FOREIGN PATENT DOCUMENTS

| | | |
|---|---|---|
| WO | 2005/012262 A1 | 2/2005 |
| WO | 2006/021458 A2 | 3/2006 |
| WO | 2009/032861 A1 | 3/2009 |
| WO | 2009/103032 A1 | 8/2009 |
| WO | 2011/046970 A1 | 4/2011 |
| WO | 2012/010826 A1 | 1/2012 |
| WO | 2012/142329 A1 | 10/2012 |
| WO | 2012/161877 A1 | 11/2012 |
| WO | 2013/024282 A2 | 2/2013 |
| WO | 2013/117285 A1 | 8/2013 |
| WO | 2014/128486 A1 | 8/2014 |

OTHER PUBLICATIONS

International Preliminary Report on Patentability issued in connection with international application No. PCT/GB2018/050475, dated Aug. 27, 2019.
International Search Report issued in connection with international application No. PCT/GB2018/050475, dated Apr. 30, 2018.

* cited by examiner

*Primary Examiner* — Amanda L Aguirre
(74) *Attorney, Agent, or Firm* — Biospark Intellectual Property Law

(57) ABSTRACT

The invention provides compounds of formula (I) wherein R is —$CH_3$ or —$CH_2CH_3$ and pharmaceutically acceptable salts thereof. The compounds of formula (I) are useful in the treatment of diseases or disorders mediated by $IKK_E$, TBK1 and/or SIK2 mechanisms in a subject, for example cancer and inflammatory and tissue repair disorders. The invention also provides uses of the compounds of formula (I) and compositions containing them. (Formula (I))

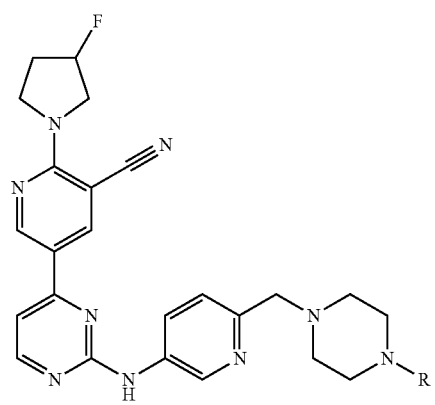

24 Claims, No Drawings
Specification includes a Sequence Listing.

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Synthesized Fluorescein-IkBalpha substrate

<400> SEQUENCE: 1

Asp Arg His Asp Ser Gly Leu Asp Ser Met Lys Asp Glu
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthesized substrate

<400> SEQUENCE: 2

Ala Met Ala Arg Ala Ala Ser Ala Ala Leu Ala Ala Arg Arg Arg
1               5                   10                  15
```

5-(PYRIMIDIN-4-YL)-2-(PYRROLIDIN-1-YL)NICOTINONITRILE COMPOUNDS AS IKKE, TBK1 AND/OR SIK2 KINASES INHIBITORS

FIELD OF INVENTION

The present invention relates to pyrimidine compounds of formula (I), compositions containing the pyrimidine compounds of formula (I), and the use of the pyrimidine compounds of formula (I) as medicaments, for example in the treatment of diseases associated with aberrant activity of the protein kinases IKKε, TBK1 and/or SIK2.

BACKGROUND

Protein kinases catalyze the phosphorylation of amino acid side chains in various substrate proteins, and play a key role in many cell functions including signal transduction, transcriptional regulation, cell motility, and cell division. There are approximately 500 different known protein kinases. Aberrant or inappropriate protein kinase activity can contribute to the development and maintenance of certain disease states.

Three protein kinases of particular relevance to this application are: I-kappa-B-kinase epsilon, IKKε, (also known as I-kappa-B-kinase-3 (IKK3) or inducible I-kappa-B-kinase (IKKi)), TANK Binding Kinase-1, TBK1 (also known as T2K or NF-kappa B-activating kinase), and salt-inducible kinase 2, SIK2 (also known as QIK or SNF1LK2). These are serine-threonine kinases that have been associated with a number of diseases, as discussed below.

IKKε and TBK1 have a high degree of sequence homology, and as a result they share a number of key biological functions. Aberrant IKKε and/or TBK1 activity can lead to various disease states. Studies have shown that IKKε inhibitors and/or dual TBK1/IKKε inhibitors may show efficacy in the treatment of certain cancers (for example breast cancer, including tamoxifen-resistant breast cancer, ovarian cancer, including cisplatin-resistant ovarian cancer, non-small cell lung cancer, and oral cancer), obesity, obesity related disorders, and in diseases in which IL-17 and/or neutrophils are believed to play an important role such as asthma, chronic obstructive pulmonary disease (COPD), psoriasis, rheumatoid arthritis and Crohn's disease. Studies have also shown that an inhibitor of TBK1 may have efficacy in the treatment of cancer. Other studies suggest that inhibitors of IKKε and TBK1 may have efficacy for the treatment/prevention of septic shock and/or the treatment of inflammatory disease.

IKKε and TBK1 are also known to play an important role in the production of type I interferons (such as interferon-beta), and the stimulation of Interferon Signature Genes (ISGs). Upregulation of type I interferons and/or this gene signature has been associated with a number of different diseases which are sometimes collectively referred to as interferonopathies (Volpi et al., *Pediatric Rheumatology*, 14:35, 2016). One such disease that shows an upregulated ISG signature is systemic lupus erythematosus (Lisnevskaia et al., *The Lancet*, 2014, 384, 1878). A dual TBK1/IKKε inhibitor has been reported to show efficacy in a Trex1 knockout mouse model (Hasan et al., *J. Immunol*, 2015, 195, 4573). These mice develop lupus-like symptoms including an elevated ISG signature as the result of the loss of the TREX1 enzyme. TREX1 mutations are found in patients with a number of auto-immune diseases such as systemic lupus erythematosus, familial chilblain lupus, and Aicardi-Goutières Syndrome; and these mutations are believe to play an important role in causing these diseases (Grieves et al., *Proc. Nat. Acad. Sci.*, 2015, 112, 5117).

SIK2 is reported to play a role in macrophage signalling pathways. SIK2 phosphorylates anti-inflammatory regulators such as CRTC3 and HDAC4, resulting in a down-regulation of the expression of anti-inflammatory cytokines such as IL-10 and an upregulation of the production of inflammatory cytokines such as IL-12 and TNF-α (Clark et al., *Proc. Natl. Acad. Sci.*, 2012, 109 (42), 16986). It is therefore believed that a SIK2 inhibitor would find application in the treatment of inflammatory disorders, including auto-immune diseases.

Disease states that may be mediated by IKKε, TBK1 and/or SIK2 mechanisms include:

inflammatory and tissue repair disorders, particularly rheumatoid arthritis, inflammatory bowel disease, asthma and chronic obstructive pulmonary disease (COPD); auto-immune diseases such as various forms of lupus (including systemic lupus erythematosus, lupus nephritis, familial chilblain lupus, and cutaneous lupus), multiple sclerosis, psoriatic arthritis, alkylosing spondylitis, Aicardi-Goutières Syndrome, and Sjögren's Syndrome; inflammation associated with infection including certain viral infections, such as acquired immune deficiency syndrome (AIDS); aberrant inflammatory responses, such as septic shock; osteoarthritis, osteoporosis and fibrotic diseases; dermatosis including psoriasis, atopic dermatitis and ultraviolet radiation (UV)-induced skin damage; tissue and organ rejection; Alzheimer's disease; stroke; atherosclerosis; restenosis; obesity; diabetes; glomerulonephritis; cancer, including Hodgkin's disease; cachexia; adult respiratory distress syndrome; Ataxia Telangiestasia, primary open angle glaucoma; and giant cell arteritis.

Certain pyrimidinyl-amines are known to act as protein kinase inhibitors. For example, WO 2005/012262, WO 2009/032861, WO 2011/046970, WO 2012/142329 and WO 2014/128486 disclose certain such compounds. In WO 2005/012262, the compounds are stated to be inhibitors of one or more of CDK1, CDK2, CDK4, CDK7, CDK9, GSK3, aurora kinase, and PLK1. In WO 2009/032861, the compounds are stated to be inhibitors of protein kinases, e.g. c-Jun N-terminal kinases (JNK). The pyrimidinyl-amines disclosed in WO 2011/046970, WO 2012/142329 and WO 2014/128486 are described as inhibitors of IKKε and/or TBK1. Surprisingly, the present inventors have now found that a certain subset of pyridine-substituted pyrimidinyl-amines having a very specific substitution pattern have especially good pharmacokinetic properties relative to the compounds previously described. They are therefore expected to find utility in patient populations where aberrant IKKε and/or TBK1 and/or SIK2 activity leads to disease, and be especially suitable for use as medicaments.

SUMMARY OF INVENTION
The present invention provides a compound of formula (I)
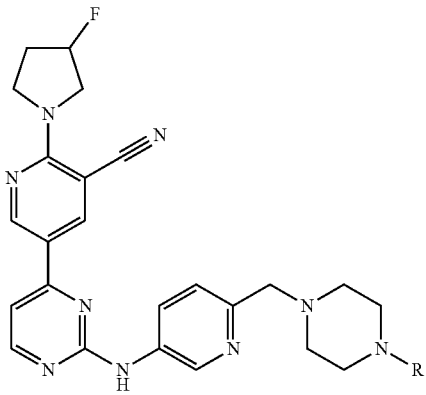
wherein R is —CH$_3$ or —CH$_2$CH$_3$.
More particularly, the present invention provides compounds of formula (Ia) and (Ib):
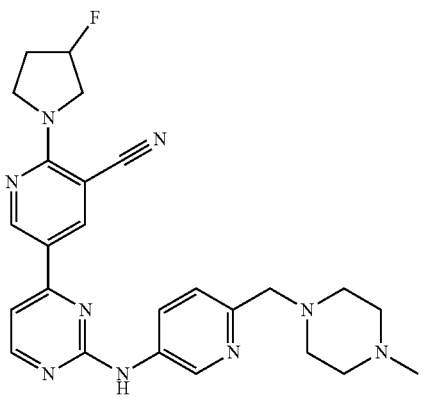
(Ia)
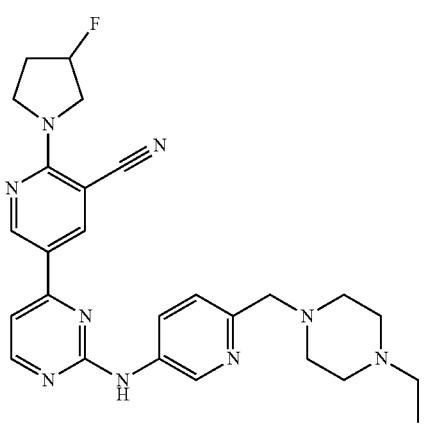
(Ib)
Even more particularly, the present invention provides a compound selected from the group consisting of:
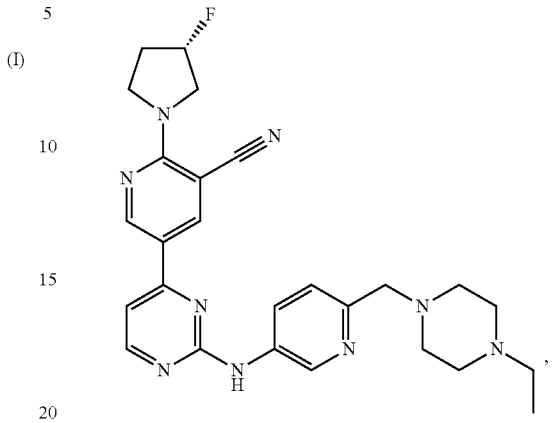
,
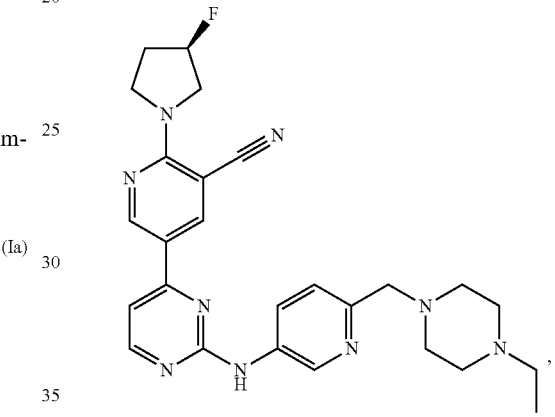
,
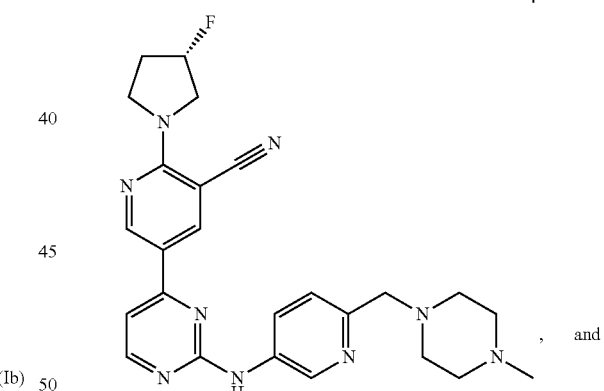
, and
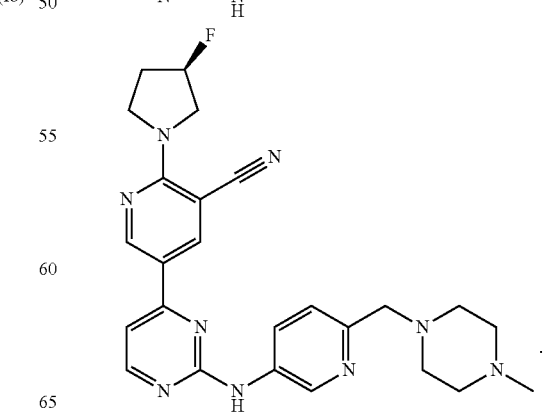
.

The compounds of the invention are inhibitors of the IKKε, TBK1 and/or SIK2 enzymes (preferably of the IKKε and/or TBK1 enzymes), and are therefore useful in the treatment of diseases associated with or caused by aberrant IKKε, TBK1 and/or SIK2 activity, and in particular aberrant IKKε and/or TBK1 activity. In addition to being very effective inhibitors of the IKKε, TBK1 and/or SIK2 enzymes, the compounds of the invention have excellent metabolic stability, and excellent in vivo pharmacokinetic properties, as shown in the Examples section, below.

In particular, it has been found by the present inventors that the compounds of the invention have a longer half-life than compounds of the prior art as a result of their larger Volume of Distribution, as shown by pharmacokinetic studies in mice. The compounds also have good hepatic stability as established in a human hepatocyte clearance assay.

An increased Volume of Distribution in one species (here the mouse) is known to be indicative of higher Volume of Distribution in other species including humans (Berry et al., *Drug Met. And Disp.*, 2011, 39, 2103). As such, the compounds of the invention are also expected to have a large Volume of Distribution and a long half-life in humans, and therefore be superior for human dosing than the compounds of the prior art.

DETAILED DESCRIPTION

The compounds of formula (I), (Ia) and (Ib) of the present invention contain a chiral (asymmetric) centre. The individual stereoisomers (enantiomers) and mixtures of these are within the scope of the present invention. Where the stereochemistry is not specifically indicated, both enantiomers are within the scope of the present invention.

In one preferred embodiment of the invention, R is —CH₃. For example, the compound of the invention is a compound of formula (Ia):

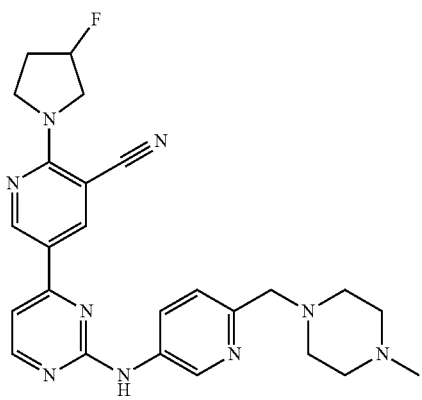

(Ia)

In embodiments where R is —CH₃, the compound of the invention may be selected from

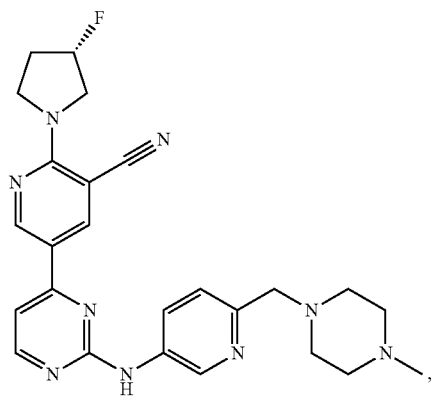

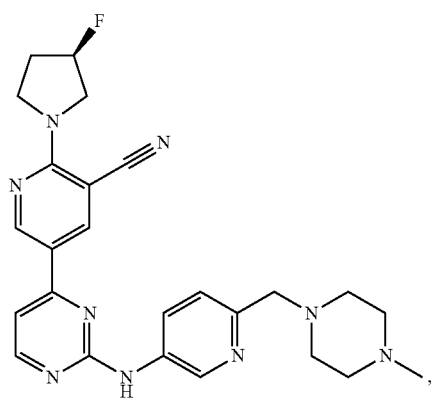

and mixtures thereof.

In another preferred embodiment of the invention, R is —CH₂CH₃. For example, the compound of the invention is a compound of formula (Ib):

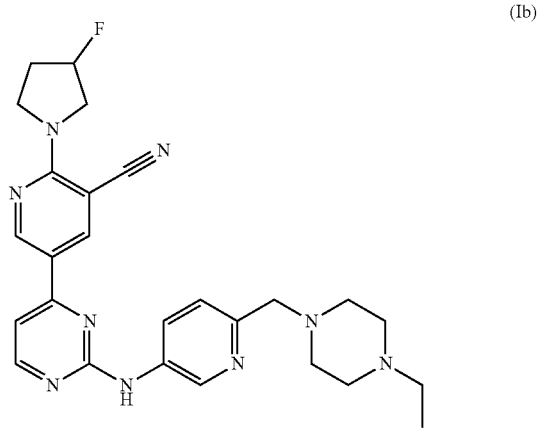 [SMILES: CCN1CCN(Cc2ccc(Nc3nccc(-c4cnc(N5CCC(F)C5)c(C#N)c4)n3)cn2)CC1]

(Ib)

In embodiments where R is —CH$_2$CH$_3$, the compound of the invention may be selected from

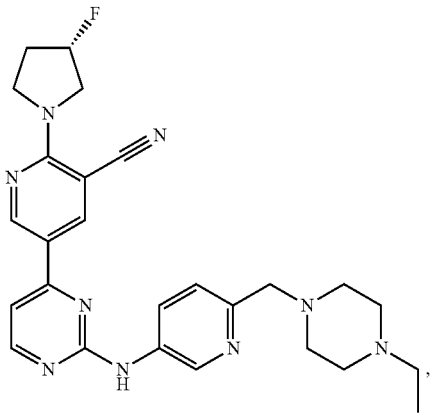

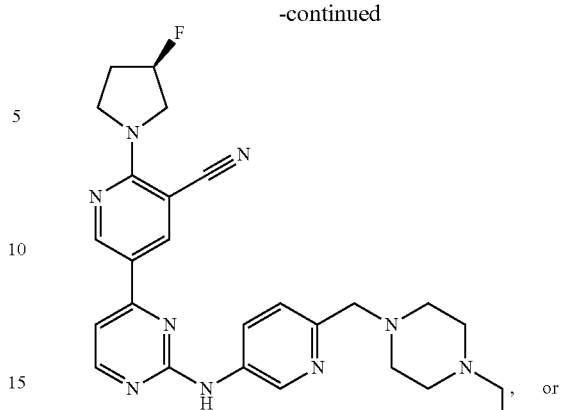

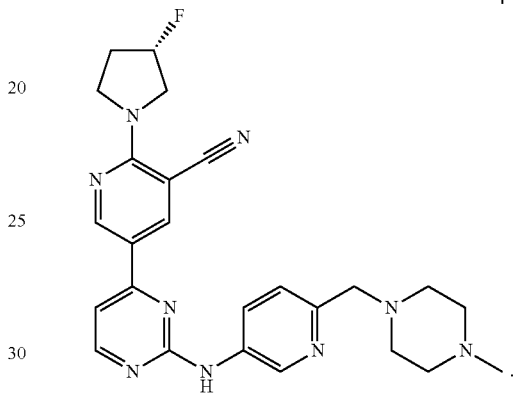

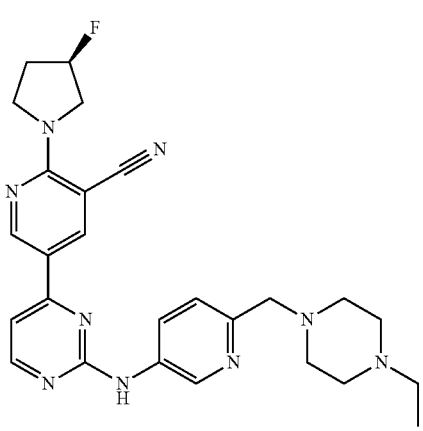

and mixtures thereof.

In one especially preferred embodiment of the invention the compound of formula (I) is

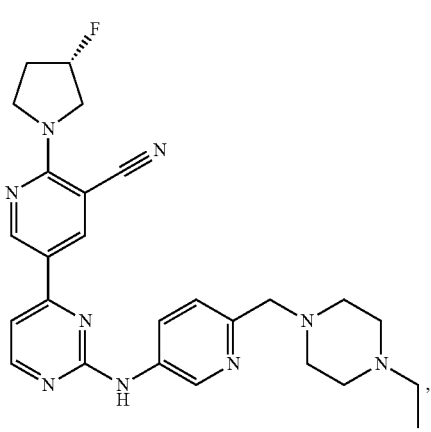 [SMILES: CCN1CCN(Cc2ccc(Nc3nccc(-c4cnc(N5CC[C@H](F)C5)c(C#N)c4)n3)cn2)CC1]

In another especially preferred embodiment of the invention the compound of formula (I) is

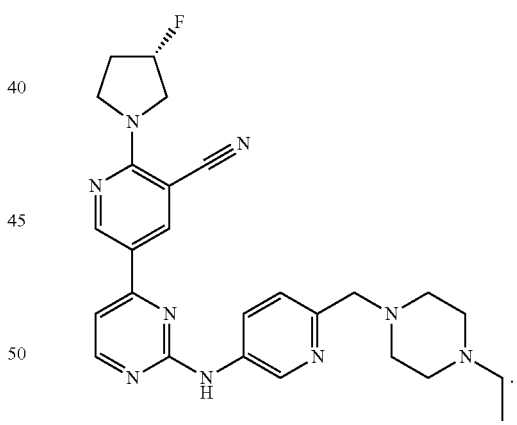

The invention includes salts of compounds of the invention. The compounds of the invention form addition salts with acids such as, for example, mineral acids, strong organic carboxylic acids, such as alkanecarboxylic acids, for example of 1 to 4 carbon atoms, which are unsubstituted or substituted, for example, by halogen, such as saturated or unsaturated dicarboxylic acids, such as hydroxycarboxylic acids, such as amino acids, or with organic sulfonic acids, such as (C$_1$-C$_4$)-alkyl- or aryl-sulfonic acids which are unsubstituted or substituted, for example by halogen. Pharmaceutically-acceptable acid addition salts generally include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Salts which are not themselves pharmaceutically acceptable, for example those derived from acids such as oxalic, may be useful as intermediates in obtaining the compounds of the invention and their pharmaceutical acceptable acid addition salts.

The compounds of the invention may also form solvates, for example hydrates, and these are also included within the scope of the present invention.

All individual stereoisomers, as well as mixtures thereof, are included within the scope of the invention. Further, isotopic forms, for example where a hydrogen atom is replaced with deuterium, are included within the invention. Certain isotopic forms may have beneficial biological properties, for example improved metabolic stability or enhanced therapeutic activity over other isotopic forms; or a specific isotopic form may be useful for biological imaging purposes, for example carbon-11, nitrogen-13 or fluorine-18 isotopic variants may be used for positron emission tomography.

Aberrant kinase activity has been implicated in many diseases. For example, c-Jun N-terminal kinases (JNK) have been implicated in diseases which involve excitotoxicity of hippocampal neurons, for example stroke, spinal cord injury, multiple sclerosis and head trauma; ischemia/reperfusion injury and conditions which may lead to or otherwise be associated with this, for example stroke, myocardial infarction, congestive heart failure, cardiac hypertrophy and atherosclerosis. JNK has also been associated with neurodegenerative diseases such as Parkinson's and Alzheimer's diseases; neural tube birth defect; chronic inflammatory diseases such as rheumatoid arthritis and atherosclerosis; obesity and insulin resistant diabetes; and cancer. It is known that for many diseases wherein individual patients display the same gross symptomology, for example breast cancer, the disease may be caused and sustained by a number of different biochemical mechanisms which will vary from patient to patient. For many such diseases, the effectiveness of any treatment will therefore be highly dependent upon the biochemical mechanisms that precipitate and maintain the diseased state.

The compounds of the invention are inhibitors of IKKε, TBK1 and/or SIK2, and are therefore useful in the treatment of diseases associated with, or caused by, aberrant IKKε, TBK1 and/or SIK2 activity. Disease states that may be mediated by IKKε, TBK1 and/or SIK2 mechanisms include: inflammatory and tissue repair disorders, for example rheumatoid arthritis, inflammatory bowel disease, asthma and chronic obstructive pulmonary disease (COPD); autoimmune diseases, for example lupus (for example systemic lupus erythematosus, lupus nephritis, familial chilblain lupus, and cutaneous lupus), multiple sclerosis, psoriatic arthritis, alkylosing spondylitis, Aicardi-Goutières Syndrome, and Sjögren's Syndrome; inflammation associated with infection, for example inflammation associated with viral infection, including acquired immune deficiency syndrome (AIDS); aberrant inflammatory responses, for example septic shock; osteoarthritis, osteoporosis and fibrotic diseases; dermatosis, for example psoriasis, atopic dermatitis and ultraviolet radiation (UV)-induced skin damage; tissue and organ rejection; Alzheimer's disease; stroke; atherosclerosis; restenosis; obesity; diabetes; glomerulonephritis; cancer, for example Hodgkin's disease; cachexia; adult respiratory distress syndrome; Ataxia Telangiestasia; primary open angle glaucoma; and giant cell arteritis.

In a preferred embodiment, the compounds of the invention are inhibitors of IKKε and/or TBK1, and are useful in the treatment of diseases associated with, or caused by, aberrant IKKε and/or TBK1 activity.

As the compounds of the invention are selective inhibitors of a small number of kinases, IKKε, TBK1 and/or SIK2, it is expected that they may be used for treatment of disease with fewer side-effects than less selective compounds. It is also expected that they will find particular utility in targeting diseases in particular patient populations, i.e. where the disease is specifically caused by aberrant IKKε and/or TBK1 and/or SIK2 activity.

In particular, the compounds of the invention are expected to be useful in the treatment of inflammatory and tissue repair disorders, particularly rheumatoid arthritis; and autoimmune diseases, particularly lupus. Sub-types of lupus include, but are not limited to, systemic lupus erythematosus, lupus nephritis, familial chilblain lupus, and cutaneous lupus. The compounds of the invention are also expected to be useful in the treatment of disease or disorders associated with increased Interferon Signature Genes (ISGs) profiles, especially autoimmune diseases, particularly lupus, and even more especially lupus with increased ISGs profiles, for example familial chilblain lupus. The compounds of the invention are also expected to be useful in the treatment of interferonopathies. Diseases grouped under the term 'interferonopathies' are diseases having in common upregulation of type I interferon and/or ISG profiles. Examples of 'interferonopathies' include familial chilblain lupus, Aicardi-Goutières Syndrome, spondyloenchondromatosis, Singleton-Merten Syndrome, and SAVI (STING-associated vasculopathy with onset in infancy).

Also, the compounds of the invention are expected to be useful in the treatment of cancer, specifically, in the treatment of patient populations in which the disease is associated with IKKε and/or TBK1 activity or with SIK2 activity. IKKε has been implicated in breast cancer, including tamoxifen resistant breast cancer, ovarian cancer, including cisplatin resistant ovarian cancer, cancer in which tumour growth and/or survival is dependent upon IKKε kinase activity, cancers harbouring Ras mutations and Ras-dependant tumours, and cancers involving amplification of the 1q32 gene locus. TBK1 has been implicated in cancers which harbour K-ras mutation and K-ras dependent tumours, cancers which harbour Ras mutations and cancers which are Ras-dependent, breast cancer, lung cancer, particularly non-small cell lung cancer (NSCLC), ovarian cancer, prostate cancer, myeloma, leukemia, oral cancer, pancreatic cancer, bowel cancer and skin cancer. SIK2 has been shown to promote growth of cancer cells, and depletion of SIK2 in cancer cells leads to a significant decrease in cancer cell growth, delayed G1/S transition and decreased phosphorylation of the apoptotic regulator AKT on serine473. Loss of SIK2 also sensitized cancer cells to the chemotherapeutic agent paclitaxel, in culture and in xenografts (Ahmed et al., Cancer Celt 2010). SIK2 has been particularly associated with the growth and spread of ovarian cancers.

In addition to cancer, specifically IKKε, TBK1, and/or SIK2 associated cancers, the compounds of the invention are expected to be particularly useful in the treatment and prevention of obesity (in which IKKε is implicated); and diseases in which hypoxia-induced angiogenesis is important, for example the treatment and prevention of septic shock, and primary open angle glaucoma (in all of which TBK1 is implicated).

The invention therefore provides a pharmaceutical composition which comprises a compound according to the invention, together with a pharmaceutically suitable carrier. Such compositions may contain the compound of the invention as the sole active agent, or they may contain a further active agent.

The invention further provides a method of treating or preventing a disease mediated by IKKε, TBK1 and/or SIK2 mechanisms (in particular a disease mediated by IKKε and/or TBK1 mechanisms; and/or in particular any of the diseases mentioned above) in a subject (preferably a human subject), which comprises administration of a compound or a composition according to the invention, to the subject; a compound or a composition according to the invention for use in therapy and/or for use as a medicament, particularly for use in the treatment or prevention of any of the diseases mentioned above; and a compound according to the invention for use in the manufacture of a medicament for use in the treatment of any of the diseases mentioned above. Preferably the compound or composition is administered to a mammal, especially a human.

Whilst a compound of the invention may be used as the sole active agent, it is also possible for the compound to be used in combination with one or more further active agents (which may also be referred to as "additional active agents"). Such further active agents may be further compounds according to the invention, or they may be different therapeutic agents, for example agents targeting one of the diseases mentioned above, and particularly the same disease as that targeted by the compound of the invention. The compound of the invention may be co-formulated with the one or more further active agent, or it may be formulated separately and administered consecutively, simultaneously or sequentially with the one or more further active agent.

The amount of active agent which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician or veterinarian can readily determine and prescribe the effective amount of the drug required to prevent, counter or arrest the progress of the condition.

Due to the excellent pharmacokinetic properties, the compound of the present invention may be provided in a lower total dosage and/or dosed less frequently than other known IKKε, TBK1 and/or SIK2 inhibitors.

Advantageously, compounds of the present invention may be administered in a single daily dose, or the total daily dosage may be administered in divided doses of two, three or four times daily.

The pharmaceutical formulations according to the invention include those suitable for oral, parenteral (including subcutaneous, intradermal, intramuscular, intravenous (bolus or infusion), and intraarticular), inhalation (including fine particle dusts or mists which may be generated by means of various types of metered doses pressurized aerosols), nebulizers or insufflators, rectal, intraperitoneal and topical (including dermal, buccal, sublingual, and intraocular) administration, although the most suitable route may depend upon, for example, the condition and disorder of the recipient. Preferred pharmaceutical formulations according to the invention are those suitable for oral and parenteral administration; and more preferably those suitable for oral administration. In another embodiment, compounds of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The formulations may conveniently be presented in unit dosage form and may be prepared by any of the methods well known in the art of pharmacy. All methods include the step of bringing the active agent into association with the carrier which constitutes one or more accessory ingredients. In general the formulations are prepared by uniformly and intimately bringing into association the active agent with liquid carriers or finely divided solid carriers or both and then, if necessary, shaping the product into the desired formulation.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, more preferably 0.1 to 5.0 mg/kg/day, and even more preferably 0.5 to 3 mg/kg/day for adult humans. An example of a daily total oral dosage may be from 1 mg to 300 mg, more preferably from about 10 mg to about 250 mg, and even more preferably from about 75 mg to about 200 mg (for example 100 mg). For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active agent for the symptomatic adjustment of the dosage to the patient to be treated. A medicament typically contains from about 0.01 mg to about 500 mg of the active agent, preferably from about 1 mg to about 300 mg of active agent, and more preferably from about 10 mg to about 250 mg of active agent, and most preferably from about 75 mg to about 200 mg of active agent (for example 100 mg of active agent). Intravenously, the most preferred doses will range from about 0.1 to about 10 mg/kg/minute during a constant rate infusion.

Formulations of the present invention suitable for oral administration may be presented as discrete units such as capsules, cachets, pills or tablets each containing a predetermined amount of the active agent; as a powder or granules; as a solution or a suspension in an aqueous liquid or a non-aqueous liquid; or as an oil-in-water liquid emulsion or a water-in-oil liquid emulsion. The active agent may also be presented as a bolus, electuary or paste.

The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or betalactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremophor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active agent in a flavoured basis such as sucrose and acacia or tragacanth, and pastilles comprising the active agent in a basis such as gelatin and glycerine or sucrose and acacia. Exemplary compositions for topical administration include a topical carrier such as Plastibase (mineral oil gelled with polyethylene).

It should be understood that in addition to the agents and/or ingredients particularly mentioned above, the formulations of this invention may include other agents conventional in the art having regard to the type of formulation in question, for example those suitable for oral administration may include flavouring agents.

EXAMPLES

The following Examples illustrate the invention.

Abbreviations Used

Ac—acetyl
aq—aqueous
CV—column volumes
dba—dibenzylideneacetone
DCM—dichloromethane
DMSO—dimethylsulfoxide
dppf—1,1'-Ferrocenediyl-bis(diphenylphosphine)
eq—equivalents
h—hours
quant—quantitative
min—minutes
TEA—triethylamine
$R_t$—retention time
Analytical Methods Used
Analytical LC-MS
HPLC Analytical Methods:
    Method A: Phenomenex Luna C18 (2) 3 µm, 50×4.6 mm; A=water+0.1% formic acid; B=MeOH+0.1%; 45° C.; % B: 0.0 min 5%, 1.0 min 37.5%, 3.0 min 95%, 3.5 min 95%, 3.51 min 5%, 4.0 min 5%; 2.25 mL/min.
    Method B: Phenomenex Luna C18 (2) 3 µm, 50×4.6 mm; A=water+0.1% formic acid; B=MeOH+0.1% formic acid; 45° C.; % B: 0.0 min 5%, 1.0 min 37.5%, 3.0 min 95%, 3.5 min 95%, 3.51 min 5%, 4.0 min 5%; 2.25 mL/min.
    Method C: Phenomenex Gemini NX C18 5 µm, 150×4.6 mm; A=water+0.1% formic acid; B=MeOH+0.1% formic acid; 40° C.; % B: 0.0 min 5%, 0.5 min 5%, 7.5 min 95%, 10.0 min 95%, 10.01 min 5%, 13 min 5%; 1.5 mL/min.
    Method D: Phenomenex Gemini NX C18 5 µm, 150×4.6 mm; A=aqueous pH9, 10 mM ammonium bicarbonate; B=MeOH; 40° C.; % B: 0.0 min 5%, 0.5 min 5%, 7.5 min 95%, 10.0 min 95%, 10.01 min 5%, 13 min 5%; 1.5 mL/min.
NMR
    NMR was also used to characterise a number of examples. NMR spectra were obtained on Bruker Advance 400, Bruker DRX 400 or Jeol 400 ECS NMR instruments at room temperature unless otherwise stated. $^1$H NMR spectra are reported in ppm and referenced to the residual solvent peaks e.g. DMSO-d6 (2.50 ppm), CDCl$_3$ (7.26 ppm) or CD$_3$OD (3.31 ppm).
Preparative HPLC Methods for Purification
    Reversed Phase Preparative HPLC-MS: Mass-directed purification by preparative LC-MS using a preparative C-18 column (Phenomenex Luna C18 (2) 5 µm, 100×21.2 mm) was used to purify a number of the examples.
    This was carried out using either acid (~pH2) or basic (~pH9) conditions
Generic Acidic Conditions:
    A=water+0.1% formic acid; B=MeOH+0.1% formic acid; 20° C.; % B: 0.0 min Initial between 2% and 50%, 0.1 min % as per Initial, 7.0 min between 40% and 95%, 9.0 min 95%, 10.0 min 95%, 10.1 min back to Initial %; 12.0 min Initial %; 20.0 mL/min.

Generic Basic Conditions:

A=water pH 9 (Ammonium Bicarbonate 10 mM); B=MeOH; 20° C.; % B: 0.0 min Initial between 2% and 50%, 0.1 min % as per Initial, 7.0 min between 40% and 95%, 9.0 min 95%, 10.0 min 95%, 10.1 min back to Initial %; 12.0 min Initial %; 20.0 mL/min.

Synthesis of Compounds of Formula (I)

Synthesis of 5-{2-[6-(4-Ethyl-piperazin-1-ylmethyl)-pyridin-3-ylamino]-pyrimidin-4-yl}-2-((S)-3-fluoro-pyrrolidin-1-yl)-nicotinonitrile (Ex. No. 1)

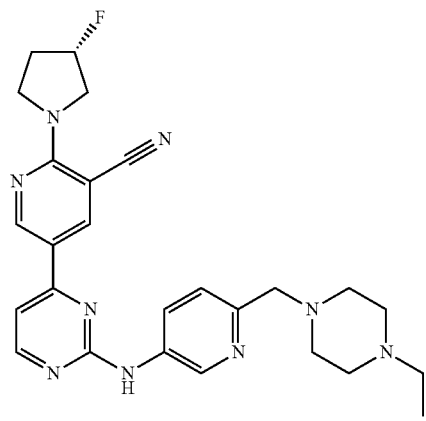

5-Bromo-2-((S)-3-fluoro-pyrrolidin-1-yl)-nicotinonitrile (Intermediate 3)

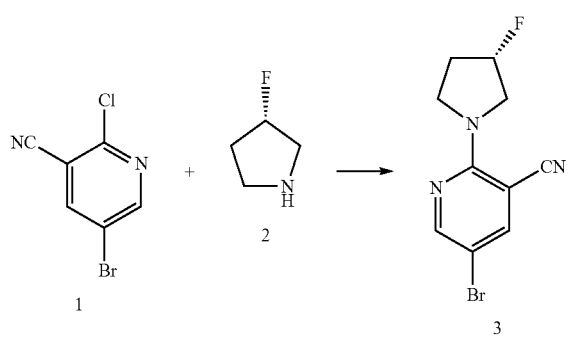 [SMILES: N#Cc1cc(Br)cnc1Cl ; F[C@H]1CCNC1 ; N#Cc1cc(Br)cnc1N1CC[C@H](F)C1]

5-Bromo-2-chloronicotinonitrile (4.10 g, 18.9 mmol, 1.0 eq), (S)-(+)-3-fluoropyrrolidine.HCl (2.50 g, 19.9 mmol, 1.05 eq) and TEA (5.30 mL, 38.0 mmol, 2.0 eq) were combined in acetonitrile (15 mL) and heated at 100° C. in a microwave for 20 min. The reaction was repeated twice on a smaller scale (5-Bromo-2-chloronicotinonitrile (2.05 g, 9.43 mmol, 1.0 eq); (S)-(+)-3-fluoropyrrolidine.HCl (1.25 g, 9.95 mmol, 1.05 eq); TEA (2.65 mL, 19.0 mmol, 2.0 eq); acetonitrile (15 mL)). The three reactions were combined and the solvent removed in vacuo. As there was still some compound 1 (5-Bromo-2-chloronicotinonitrile) remaining the residue was dissolved in dry acetonitrile (100 mL), (S)-(+)-3-fluoropyrrolidine.HCl (0.489 g, 3.9 mmol) and TEA (10.0 mL, 71.7 mmol) added and the mixture heated at 100° C. for 4 h. The reaction was allowed to cool to room temperature and solvent removed in vacuo. The residue was dissolved in DCM (250 mL) and washed with 0.1 N HCl (200 mL) then brine (200 mL). The organic phase was dried over MgSO$_4$, filtered and the solvent removed in vacuo to yield intermediate 3 as a pale brown solid (9.60 g, 94.0% yield); LC-MS R$_t$=3.15 min (Method A), m/z 270 (MH$^+$).

5-(2-Chloro-pyrimidin-4-yl)-2-((S)-3-fluoro-pyrrolidin-1-yl)-nicotinonitrile (Intermediate 4)

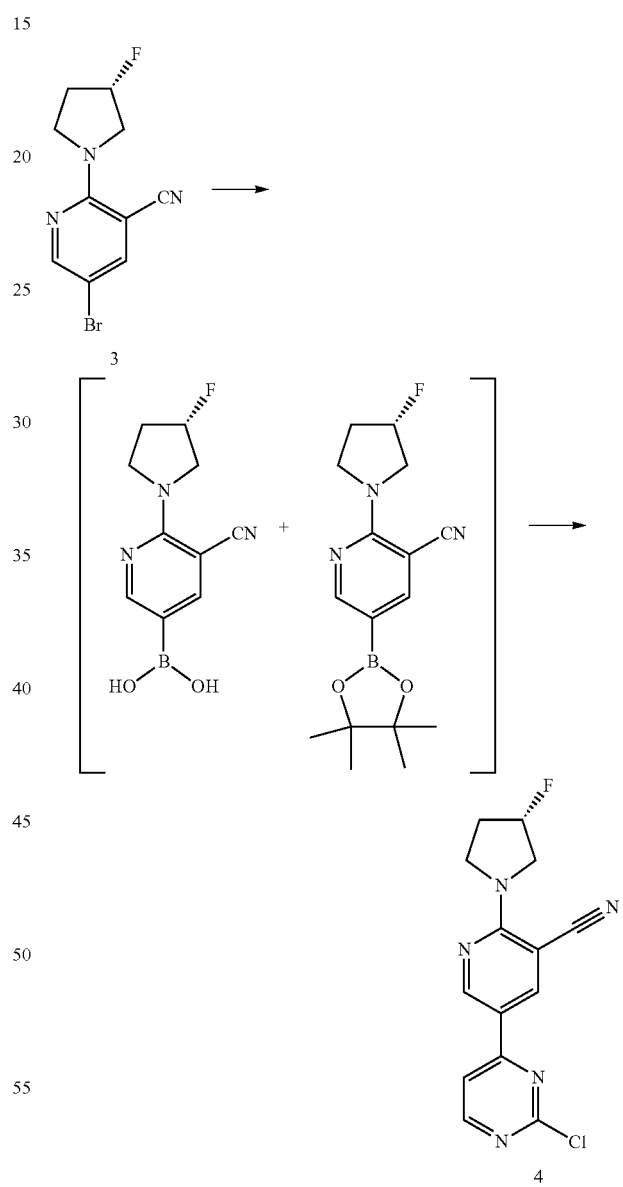

Intermediate 3 (9.60 g, 35.5 mmol, 1.0 eq), bis-pinacolatodiboron (10.8 g, 42.5 mmol, 1.2 eq) and KOAc (6.98 g, 71.1 mmol, 2.0 eq) were dissolved in 1,4-dioxane (250 mL). The mixture was de-oxygenated with N$_2$ (g) for 15 min. Pd(dppf)Cl$_2$.DCM (1.45 g, 1.78 mmol, 5 mol %) was added and the solution was heated to reflux for 3 h. Intermediate boronic acid and boronic ester were formed (LCMS R$_t$=2.34 min and 3.37 min (Method B), m/z=236 and 318). K₂CO₃ (9.81 g, 71.1 mmol, 2.00 eq), 2,4-dichloropyrimidine (5.82 g, 39.1 mmol, 1.10 eq), Pd(PPh₃)₃ (3.25 g, 2.8 mmol, 8 mol %) and H₂O (125 mL) were added to the reaction and the mixture was heated at 100° C. for a further 2 h. The mixture was allowed to cool to room temperature and the solution left standing for 16 h. The solvent was removed in vacuo, diluted with DCM (400 mL) and H₂O (200 mL) and the layers separated. The organic layer was washed with brine (200 mL), dried over MgSO₄, filtered and the solvent removed in vacuo. The crude product was purified by flash column chromatography (Biotage SNAP cartridge, 25% ethylacetate in isohexane to 50% ethylacetate in isohexane). The fractions that contained the desired material were combined and solvent removed in vacuo. Analysis of the fractions showed the presence of triphenylphosphine oxide. The crude compound (8.90 g) was separated into 3 batches and each purified individually by flash column chromatography (Biotage SNAP cartridge 100 g, 20% ethyl acetate in isohexane to 50% ethylacetate in isohexane). The solvent was removed in vacuo and the three batches of Intermediate 4 combined to yield a yellow solid (7.77 g, 72%); LC-MS $R_t$=3.08 min (Method B), m/z 304 (MH⁺).

5-Bromo-2-bromomethyl-pyridine (Intermediate 6)

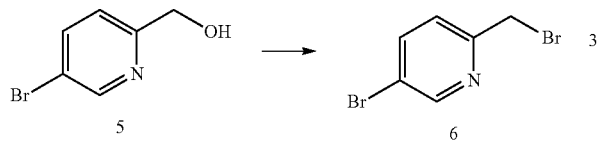

5-Bromo-2-(hydroxymethyl)pyridine (14.0 g, 74.5 mmol, 1.0 eq) was dissolved in acetonitrile (200 mL) and phosphorous tribromide (9.0 mL, 97.0 mmol, 1.30 eq) was added dropwise over 10 minutes to give a white suspension. The resulting mixture was stirred at room temperature over 48 h. Water was added (15 mL) before neutralising the reaction mixture with 50% NaOH (aq) until pH 7 was achieved. Water (100 mL) and DCM (200 mL) were added and the mixture separated. The aqueous layer was washed with DCM (200 mL). The combined organic layers were dried over MgSO₄, filtered and the solvent removed in vacuo to yield a purple oil (18.5 g, 99.5%); LC-MS $R_t$=2.71 min (Method B), m/z 250, 252 (MH⁺). Intermediate 6 was used without further purification in future reactions.

1-(5-Bromo-pyridin-2-ylmethyl)-4-ethyl-piperazine (Intermediate 7)

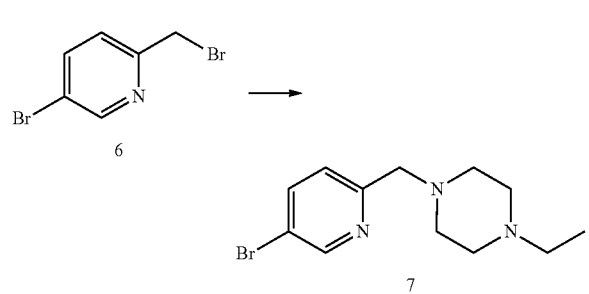

To a stirred solution of intermediate 6 (18.5 g, 74.0 mmol, 1.0 eq) in acetonitrile (150 mL) was added N-ethylpiperazine (10.3 mL, 81.0 mmol, 1.1 eq) and TEA (31.0 mL, 222 mmol, 3.0 eq) and the solution was stirred at room temperature for 2.5 h. The solvent was removed in vacuo and the crude product was purified by flash column chromatography (Biotage KP-Sil cartridge 340 g, 0% to 15% methanol in DCM with 1% TEA). Fractions containing the desired product were combined and the solvent removed in vacuo. The product was further dried in vacuo for 48 h to yield intermediate 7 as a brown solid (15.2 g, 72.3%); LC-MS $R_t$=1.15 min (Method A), m/z 284,286 (MH⁺).

Benzhydrylidene-[6-(4-ethyl-piperazin-1-ylmethyl)-pyridin-3-yl]-amine (Intermediate 8)

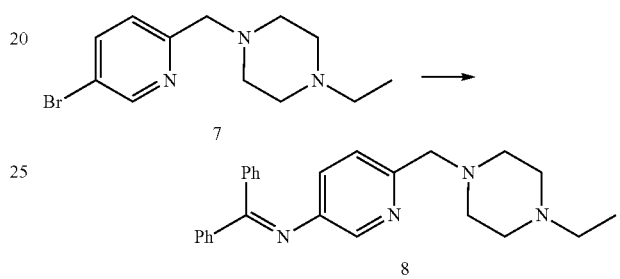

Intermediate 7 (15.2 g, 53.4 mmol, 1.0 eq), benzophenoneimine (11.7 mL, 69.5 mmol, 1.30 eq), Pd(OAc)₂ (599 mg, 2.67 mmol, 5 mol %), Xantphos (1.34 g, 4.81 mmol, 9 mol %) and KO$^t$Bu (9.0 g, 80.2 mmol, 1.50 equiv) were combined in 1,4-dioxane (150 mL) and the mixture deoxygenated with N₂ (g) for 20 mins before heating to 120° C. for 5 h. Extra Pd(OAc)₂ (120 mg, 1 mol %), Xantphos (148 mg, 1 mol %) and KO$^t$Bu (359 mg, 6 mol %) were added and the mixture stirred at 120° C. for 1 h. The reaction was allowed to cool to room temperature, diluted with H₂O (50 mL) and the product extracted into ethylacetate (2×100 mL). The combined organic layers were dried over MgSO₄, filtered and the solvent was removed in vacuo. The desired target intermediate 8 was obtained as a dark brown oil (21.5 g, quant); LC-MS $R_t$=2.13 min (Method B), m/z 385 (MH⁺). Intermediate 8 was used without further purification in future reactions.

6-(4-Ethyl-piperazin-1-ylmethyl)-pyridin-3-ylamine (Intermediate 9)

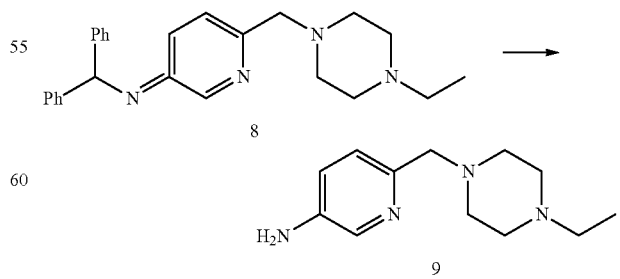

Intermediate 8 (21.5 g, 55.9 mmol, 1.0 eq) hydroxylamine.HCl (7.80 g, 112 mmol, 2.0 eq) and sodium acetate (11.5 g, 139 mmol, 2.5 eq) were combined in ethanol (200 mL) and stirred at room temperature for 2 h. The mixture was filtered and the solvent removed in vacuo to yield a brown oil. This was partitioned between ethyl acetate (100 mL) and 0.5M NaOH (aq) (50 mL) and separated. The combined organics were washed with 0.5M NaOH (aq) (50 mL) and the combined aqueous washed with ethyl acetate (3×100 mL). The aqueous layer was neutralised with 0.5 N HCl (aq) and the solvent was removed in vacuo to yield a yellow solid. This was dissolved in methanol and passed through a catch-release cartridge (Biotage SCX-2; 50 g) washing with methanol (4 CV) and eluting with 1.0 M $NH_3$/methanol (4 CV). The solvent was removed in vacuo to yield the crude product. This was dissolved in DCM and purified by flash column chromatography (Biotage KP-Sil cartridge 340 g, 5% methanol in DCM 1% TEA to 15% methanol in DCM 1% TEA). The fractions were analysed and those containing the desired material were combined and the solvent removed in vacuo to yield intermediate 9 as a yellow oil, which solidified upon standing, to form a yellow wax (2.12 g, 18%); LC-MS $R_t$=1.79 min (Method B), m/z 221 (MH⁺).

5-{2-[6-(4-Ethyl-piperazin-1-ylmethyl)-pyridin-3-ylamino]-pyrimidin-4-yl}-2-((S)-3-fluoro-pyrrolidin-1-yl)-nicotinonitrile (Ex. No. 1)

Intermediate 4 (1.6 g, 5.3 mmol, 1.0 eq), Intermediate 9 (1.4 g, 6.4 mmol, 1.2 eq), $Pd_2(dba)_3$ (480 mg, 0.53 mmol, 10 mol %), Davephos (400 mg, 1.05 mmol, 20 mol %) and NaOtBu (760 mg, 7.9 mmol, 1.5 eq) were combined in 1,4-dioxane (30 mL) and the mixture de-oxygenated with $N_2$ for 15 mins before heating in a microwave at 120° C. for 20 min. The mixture was loaded onto silica and purified by flash column chromatography (Biotage KP-Sil cartridge, 100 g, eluting with 5% (0.7 M $NH_3$ in methanol)/dichloromethane) to give the desired product as an orange solid (1.4 g). This material was further purified by reversed phase preparative LC-MS (pH2), followed by evaporation of the solvent and lyophilisation to give Ex. No. 1 as white solid (650 mg, 23%). Ex. No. 1 was isolated as the formic acid salt; LC-MS $R_t$=8.09 min (Method D), $R_t$=5.06 min (Method C), m/z 488 (MH⁺); ¹H NMR (400 MHz, DMSO-d₆): δ 9.80 (1H, s), 9.12 (1H, d, J=2.3 Hz), 8.86 (1H, d, J=2.5 Hz), 8.69 (1H, d, J=2.3 Hz), 8.51 (1H, d, J=5.3 Hz), 8.19 (1H, s), 8.15 (1H, dd, J=8.4, 2.5 Hz), 7.45 (1H, d, J=5.3 Hz), 7.36 (1H, d, J=8.4 Hz), 5.49 (1H, d, J=52.8 Hz), 4.11-3.90 (3H, m), 3.89-3.70 (1H, m), 3.53 (2H, s), 2.49-2.30 (10H, m), 2.30-2.10 (2H, m), 0.98 (3H, t, J=7.1 Hz).

Synthesis of 5-{2-[6-(4-Ethyl-piperazin-1-ylmethyl)-pyridin-3-ylamino]-pyrimidin-4-yl}-2-((R)-3-fluoro-pyrrolidin-1-yl)-nicotinonitrile (Ex. No. 2)

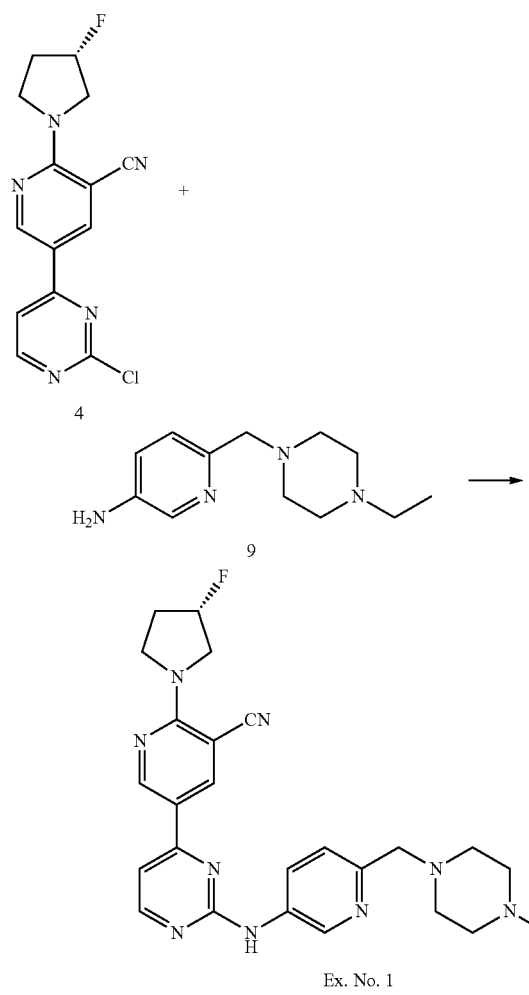

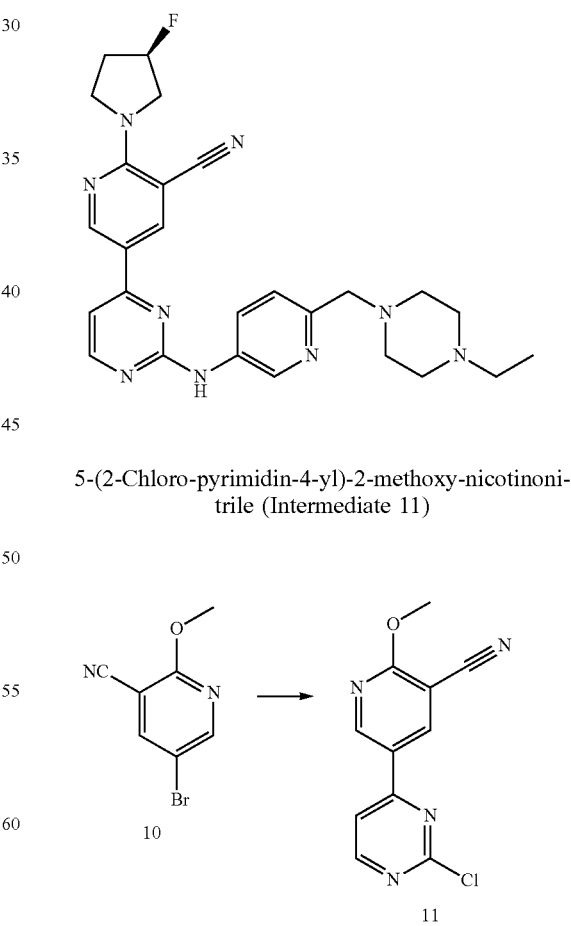

5-(2-Chloro-pyrimidin-4-yl)-2-methoxy-nicotinonitrile (Intermediate 11)

5-Bromo-2-methoxynicotinonitrile (10) (12.5 g, 58.7 mmol, 1.0 eq), bis-pinacolatodiboron (17.9 g, 70.4 mmol, 1.2 eq) and KOAc (8.6 g, 88.0 mmol, 1.5 eq) were combined in 1,4-dioxane (140 ml) and the solution was de-oxygenated with N₂ for 25 mins. Pd(dppf)Cl₂ (1.30 g, 1.76 mmol, 3 mol %) was added and the resulting solution heated at 100° C. for 2 h. 2,4-Dichloropyrimidine (9.6 g, 64.5 mmol, 1.1 eq), K₂CO₃ (16.2 g, 117 mmol, 2.0 eq), Pd(PPh₃)₃ (3.4 g, 2.94 mmol, 5 mol %) and H₂O (100 mL) were added and the solution heated at 100° C. for 1.5 h. The mixture was allowed to cool to room temperature before diluting further with H₂O (50 mL). The product was extracted into DCM (3×100 mL) and the combined organic layers passed through a phase separator. The solvent was removed in vacuo. The crude product was recrystallized from iso-propanol, then filtered and dried in vacuo to yield intermediate 11 as a brown solid (11.3 g, 78%); LC-MS R$_t$=2.88 min (Method B), m/z=247 (MH⁺).

5-{2-[6-(4-Ethyl-piperazin-1-ylmethyl)-pyridin-3-ylamino]-pyrimidin-4-yl}-2-methoxy-nicotinonitrile (Intermediate 12)

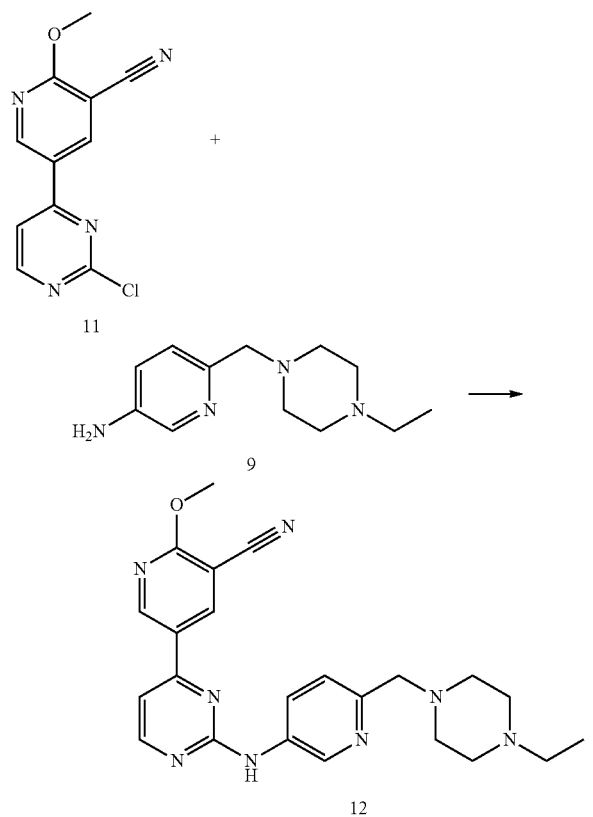

Intermediate 11 (862 mg, 3.49 mmol, 1.10 eq), intermediate 5 (700 mg, 3.18 mmol, 1.0 eq), Pd₂(dba)₃ (290 mg, 0.32 mmol, 10 mol %), Davephos (250 mg, 0.64 mmol, 20 mol %) and NaOtBu (336 mg, 3.5 mmol, 1.1 eq) were combined in 1,4-dioxane (15 mL). The mixture was de-oxygenated with N₂ before heating to 100° C. in a microwave for 15 mins. The solvent was removed in vacuo and the resulting residue dissolved in methanol. This solution was passed through a catch-release cartridge (Biotage, SCX-2; 25 g) washing with methanol (4 CV) and eluting with 1 M NH₃/methanol (4 CV). The solvent was removed in vacuo to yield the crude product as a brown foam. This was purified by flash column chromatography (Biotage KP-Sil cartridge 50 g, 0% MeOH in DCM to 20% MeOH in DCM). Fractions containing the desired material were combined and the solvent was removed in vacuo to yield the desired target intermediate 12 as a light brown solid (1.30 g, quant); LC-MS R$_t$=1.84 mins (Method B), m/z 431 (MH⁺).

5-{2-[6-(4-Ethyl-piperazin-1-ylmethyl)-pyridin-3-ylamino]-pyrimidin-4-yl}-2-hydroxy-nicotinonitrile (Intermediate 13)

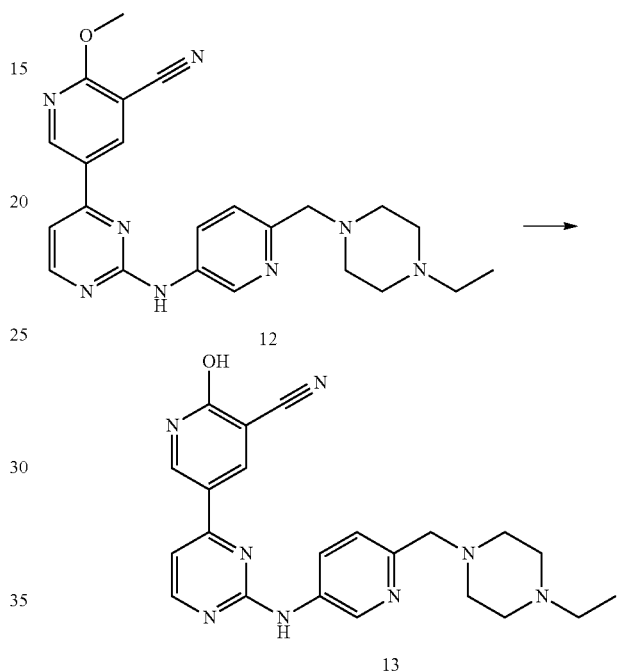

Intermediate 12 (500 mg, 1.16 mmol, 1.0 eq) was dissolved in 4 N HCl in dioxane (10 mL) and H₂O (5 mL) and the mixture heated to 100° C. in a microwave for 15 min. The solvent was removed in vacuo and the residue triturated with 80% methanol/DCM. The solvent was removed in vacuo to yield the desired intermediate 13 as a light brown solid (1.02 g, quant); LC-MS R$_t$=1.37 mins (Method B), m/z 417 (MH⁺).

2-Chloro-5-{2-[6-(4-ethyl-piperazin-1-ylmethyl)-pyridin-3-ylamino]-pyrimidin-4-yl}-nicotinonitrile (Intermediate 14)

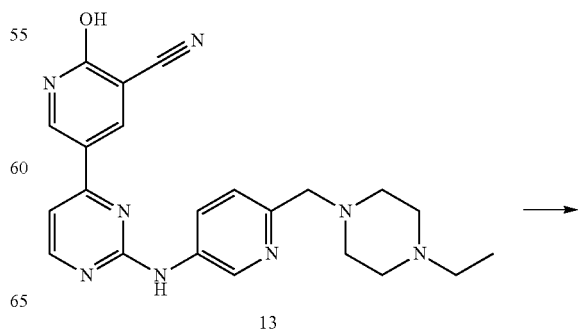

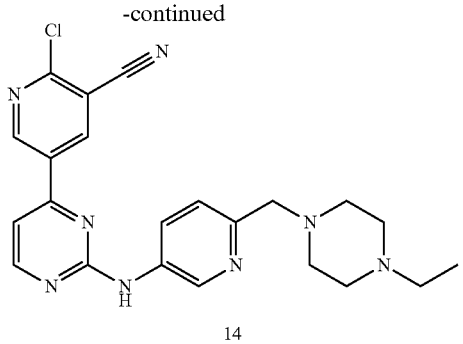

14

Intermediate 13 (5.60 g, 13.5 mmol, 1.0 eq) was mixed with POCl₃ (30 mL) and the resulting suspension was heated to 110° C. for 3 h. The reaction mixture was added dropwise to an ice-water solution over 45 min and then neutralised with 0.5 M NaOH (aq) until pH 7 was achieved. A gel formed which was diluted with H₂O (100 mL) and DCM (100 mL). The mixture was separated and the aqueous layer washed further with DCM (2×200 mL). The combined organics were dried over MgSO₄, filtered and solvent removed in vacuo. The crude product purified by flash column chromatography (Biotage KP-Sil cartridge 50 g, 0% MeOH in DCM with 1% TEA to 20% MeOH in DCM with 1% TEA). Fractions containing the desired material combined and solvent removed in vacuo to yield intermediate 14 as a yellow solid (250 mg, 10%); LC-MS $R_f$=1.75 mins (Method A), m/z 435 (MH⁺).

5-{2-[6-(4-Ethyl-piperazin-1-ylmethyl)-pyridin-3-ylamino]-pyrimidin-4-yl}-2-((R)-3-fluoro-pyrrolidin-1-yl)-nicotinonitrile (Ex. No. 2)

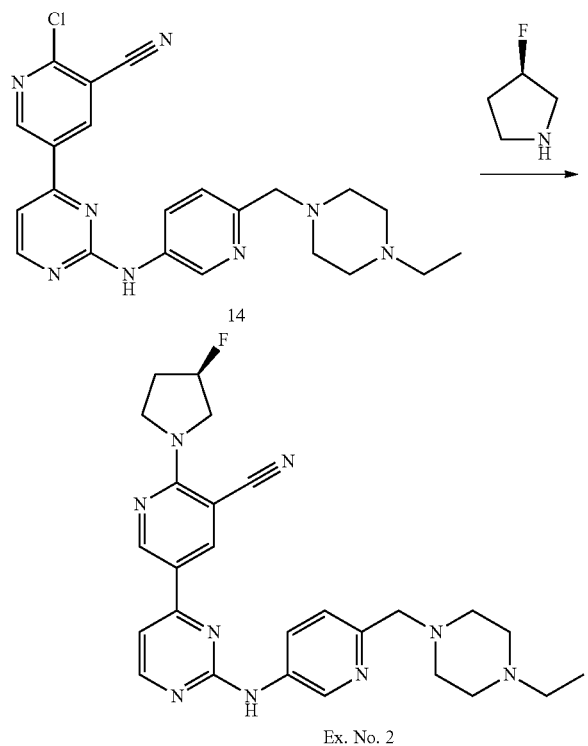

Intermediate 14 (85.0 mg, 0.20 mmol, 1.0 eq) was combined with (R)-fluoropyrrolidine (27.0 mg, 0.22 mmol, 1.1 eq) and TEA (82.0 µL, 0.59 mmol, 3.0 eq) in acetonitrile (2 mL) and the mixture heated in the microwave at 100° C. for 1 h. The solvent was removed in vacuo and the crude product redissolved in methanol. This solution was passed through a catch-release cartridge (Biotage SCX-2; 5 g) washing with methanol (4 CV) and eluting with 1.0 M NH₃/methanol (4 CV). The solvent was removed in vacuo and the residue dissolved in DMSO (2 mL) and purified by reversed phase LC-MS at pH9. Fractions containing the desired product were combined and the solvent removed in vacuo. The residue was dissolved in 1:1 H₂O/acetonitrile, frozen (−78° C.) and the solvent removed by lyophilisation to yield Ex. No. 2, as an off-white solid (31.0 mg, 38%); LC-MS $R_t$=8.10 min (Method D), $R_t$=5.05 min (Method C) m/z 488 (MH⁺); ¹H NMR (400 MHz, DMSO-d₆): δ 9.79 (1H, s), 9.13 (1H, d, J=2.3 Hz), 8.86 (1H, d, J=1.8 Hz), 8.69 (1H, d, J=1.8 Hz), 8.51 (1H, d, J=5.5 Hz), 8.15 (1H, dd, J=8.7, 2.3 Hz), 7.46 (1H, d, J=5.5 Hz), 7.36 (1H, d, J=8.7 Hz), 5.49 (1H, d, J=53.1 Hz), 4.12-3.90 (3H, m), 3.89-3.79 (1H, m), 3.53 (2H, s), 2.48-2.10 (12H, m), 0.96 (3H, t, J=7.1 Hz).

Synthesis of 2-((S)-3-Fluoro-pyrrolidin-1-yl)-5-{2-[6-(4-methyl-piperazin-1-ylmethyl)-pyridin-3-ylamino]-pyrimidin-4-yl}-nicotinonitrile (Ex. No. 3)

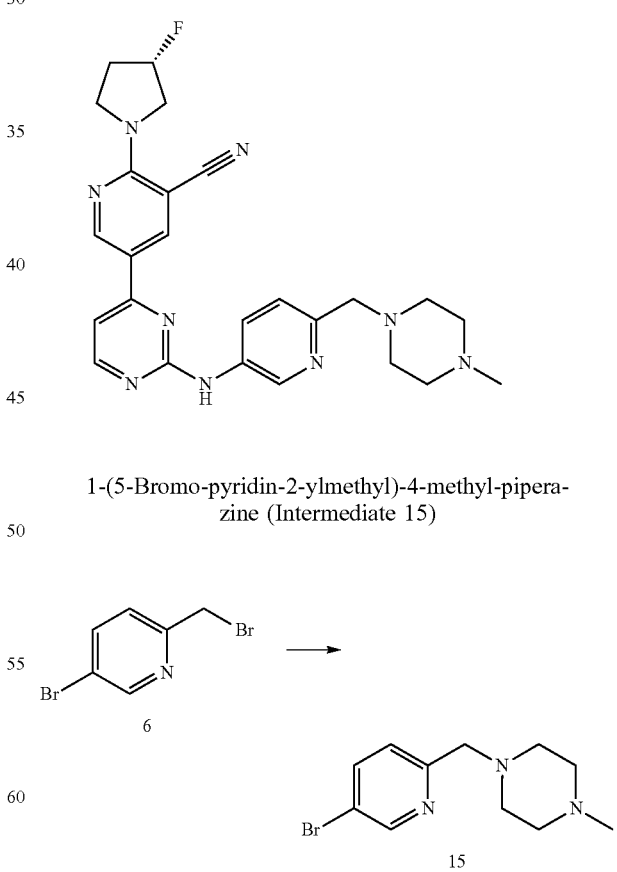

1-(5-Bromo-pyridin-2-ylmethyl)-4-methyl-piperazine (Intermediate 15)

To a stirred solution of intermediate 6 (750 mg, 3.0 mmol, 1.00 eq) in acetonitrile (15 mL) was added N-methylpiperazine (400 µL, 3.6 mmol, 1.2 eq) and TEA (1.25 mL, 9.0 mmol, 3.0 eq) and the mixture stirred at room temperature for 1 h. The solvent was removed in vacuo. The resulting solid was dissolved in methanol and passed through a catch-release cartridge (Biotage SCX-2; 25 g), washing with methanol (4 CV) and eluting with 1 M $NH_3$ in methanol (4 CV). The solvent was removed in vacuo to yield intermediate 15 as a dark red oil (688 mg, 85%); LC-MS $R_t$=1.11 min (Method B), m/z 270 (MH$^+$). This was used without further purification in the next step.

Benzhydrylidene-[6-(4-methyl-piperazin-1-ylmethyl)-pyridin-3-yl]-amine (Intermediate 16)

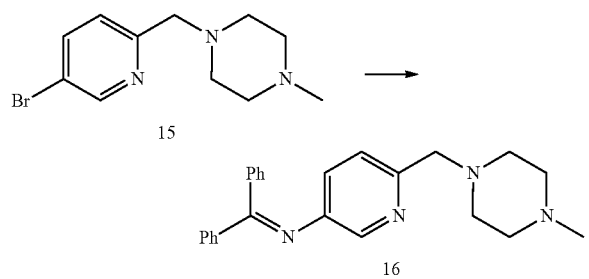

Intermediate 16 (688 mg, 2.6 mmol, 1.0 eq), benzophenoneimine (555 µL, 3.3 mmol, 1.3 eq), Pd(OAc)$_2$ (28.5 mg, 0.13 mmol, 5 mol %), Xantphos (132 mg, 0.23 mmol, 9 mol %) and KO$^t$Bu (428 mg, 3.8 mmol, 1.5 equiv) were combined in 1,4-dioxane (10 mL) and the mixture de-oxygenated with N$_2$ for 15 mins before heating to 120° C. for 3 h. The reaction was diluted with H$_2$O (50 mL) and the product extracted into EtOAc (3×50 mL). The combined organic layers were dried over MgSO$_4$, filtered and the solvent was removed in vacuo. The resulting crude material was purified by flash column chromatography (Biotage KP-Sil cartridge, DCM to 20% methanol in DCM, product eluted at 16% methanol). Fractions containing the desired material were combined and the solvent was removed in vacuo to yield intermediate 16 as a yellow oil (233 mg, 25%); LC-MS $R_t$=2.15 min (Method A), m/z 371 (MH$^+$).

6-(4-Methyl-piperazin-1-ylmethyl)-pyridin-3-ylamine (Intermediate 17)

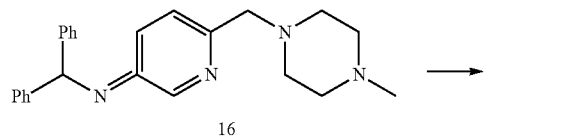

Intermediate 16 (233 mg, 0.63 mmol, 1.0 eq), hydroxylamine.HCl (88 mg, 1.26 mmol, 2.0 eq) and sodium acetate (129 mg, 1.57 mmol, 2.5 eq) were combined in ethanol (10 mL) and stirred at room temperature for 3 h. The solvent was removed in vacuo and the residue dissolved in methanol. This solution was passed through a catch-release cartridge (Biotage SCX-2; 5 g) washing with methanol (4 CV) and eluting with 1.0 M NH$_3$ in methanol (4 CV). The solvent was removed in vacuo to yield intermediate 17 as a light yellow oil (110 mg, 85%); LC-MS $R_t$=0.24 min (Method B), m/z 207 (MH$^+$).

2-((S)-3-Fluoro-pyrrolidin-1-yl)-5-{2-[6-(4-methylpiperazin-1-ylmethyl)-pyridin-3-ylamino]-pyrimidin-4-yl}-nicotinonitrile (Ex. No. 3)

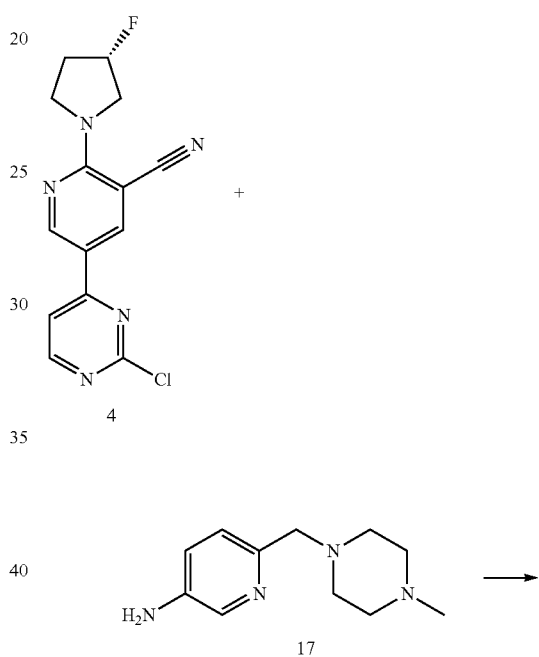

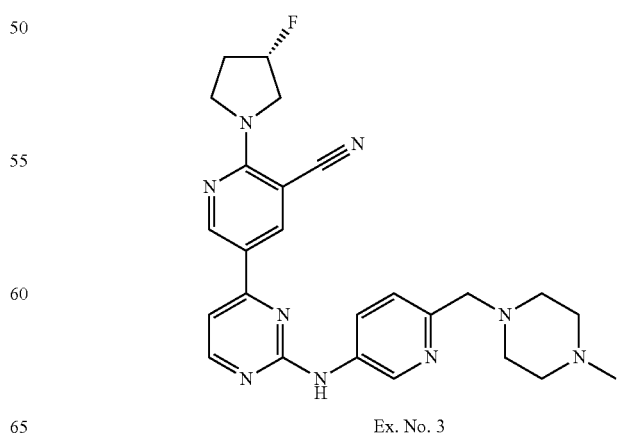

Intermediate 4 (60 mg, 0.20 mmol, 1.0 eq), intermediate 17 (45 mg, 0.22 mmol, 1.1 eq), Pd$_2$(dba)$_3$ (18.0 mg, 0.02 mmol, 10 mol %), Davephos (16.0 mg, 0.04 mmol, 20 mol %) and NaO$^t$Bu (21 mg, 0.22 mmol, 1.1 eq) were combined in 1,4-dioxane (2 mL) and the mixture de-oxygenated with N$_2$ for 15 mins before heating in the microwave at 100° C. for 15 mins. The solvent was removed in vacuo and the residue dissolved in methanol. This solution was passed through a catch-release cartridge (biotage SCX-2; 5 g) washing with methanol (4 CV) and eluting with 1.0 M NH$_3$ in methanol (4 CV). The solvent was removed in vacuo. The crude product was dissolved in DMSO (1 mL) and purified by reversed phase preparative LC-MS at pH2. Fractions containing the desired product were combined and the solvent removed in vacuo. The residue was dissolved in 1:1 H$_2$O/acetonitrile, frozen (−78° C.) and the solvent removed by lyophilisation to yield Ex. No. 3 as a yellow solid (35.0 mg, 38.0%). Ex. No. 3 was isolated as the formic acid salt; LC-MS R$_t$=7.97 min (Method D), R$_t$=4.99 min (Method C) m/z 474 (MH$^+$); $^1$H NMR (400 MHz, DMSO-d$_6$): δ 9.79 (1H, s), 9.13 (1H, d, J=2.3 Hz), 8.86 (1H, d, J=2.8 Hz), 8.69 (1H, d, J=2.3 Hz), 8.52 (1H, d, J=5.3 Hz), 8.17 (1H, s), 8.15 (1H, dd, J=8.7, 2.8 Hz), 7.46 (1H, d, J=5.3 Hz), 7.36 (1H, d, J=8.7 Hz), 5.49 (1H, d, J=53.1 Hz), 4.12-3.90 (3H, m), 3.89-3.79 (1H, m), 3.53 (2H, s), 2.47-2.13 (10H, m), 2.19 (3H, s).

Biological Testing

Ex. No. 1 and Ex. No. 3 were tested as their formic acid salts. Ex. No. 2 was tested as the free base.

IKKε and TBK1 Enzyme Potency

Compounds of the invention (synthesised as described above), and Comparative Examples 1 to 5 (which may be synthesised as described in WO 2014/128486), were tested for potency against the IKKε and TBK1 enzyme as follows:

Inhibition studies were performed using a time-resolved fluorescence-based Lanthascreen™ assay. Phosphorylation of a fluorescein-labelled substrate peptide is measured using terbium-labeled phosphospecific antibodies. Terbium is excited at 340 nm and the FRET energy transfer to fluorescein is measured at 495 and 520 nm. The emission ratio between 520 and 495 is a measure of the level of phosphorylation of the substrate by the kinase.

Kinase inhibition assays (5 μL) were performed at 20° C. in 384-well plate format. Compound IC$_{50}$ values were determined at the apparent Km for ATP (20 μM) based on a radiometric assay (Invitrogen) using 8 or 10 point curves in duplicate. The final reaction conditions contained 380 nM fluorescein-IkBα substrate (DRHD$\underline{S}$GLDSMKDE) [SEQ ID No 1], 20 μM ATP, 0.9-3 nM IKKε or or 6-8 nM TBK1 kinase respectively, and 1% DMSO in kinase assay buffer consisting of 50 mM HEPES (pH 7.5), 10 mM MgCl$_2$, 1 mM EGTA, 0.05% Brij-35.

Compound dilutions were prepared from 10 mM DMSO stocks by dilution into DMSO. Compound dilution series were further diluted in kinase assay buffer to give a 5% DMSO stock, the final concentration in the assay being 1% DMSO.

The kinase phosphorylation assay was initiated by the addition of the kinase and the reaction was allowed to proceed for 1 h or 2.5 h for IKKε and TBK1 kinase respectively. Both conditions were within the linearity of the phosphorylation. The reaction was stopped by the addition of 10 mM EDTA, and phosphorylation was detected after a 1 hour incubation with 1.5 nM terbium-labelled antibody against phosphorylation at Serine 32 on the IkBα peptide, both in TR-FRET dilution buffer (Invitrogen).

SIK2 was measured using radiolabelled $^{33}$P-ATP using the Kinase HotSpot$^{SM}$ technology of Reaction Biology Corporation. The peptide AMARAASAALAARRR [SEQ ID No 2] at a concentration of 20 μM was used as the substrate. IC$_{50}$ values were determined at the apparent Km for ATP (30 μM)

The enzyme potency for IKKε, TBK1 and SIK2 for the exemplified compounds of the invention are shown in Table 1, below. The example compounds of invention have high enzyme potency against IKKε (i.e. an IC$_{50}$<25 nM for IKKε), TBK1 (i.e. an IC$_{50}$ of <20 nM for TBK1) and SIK2.

TABLE 1

| Ex. No. | Structure | Inhibition of IKKε | Inhibition of TBK1 | Inhibition of SIK2 |
|---|---|---|---|---|
| 1 | 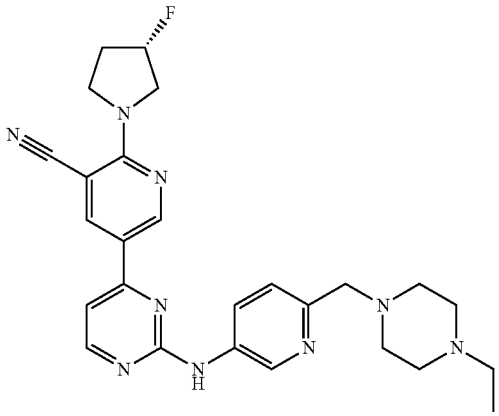 [SMILES: CCN1CCN(Cc2ccc(Nc3nccc(-c4cnc(N5CC[C@H](F)C5)c(C#N)c4)n3)cn2)CC1] | 16 nM | 9 nM | 7 nM |

TABLE 1-continued

| Ex. No. | Structure | Inhibition of IKKε | Inhibition of TBK1 | Inhibition of SIK2 |
|---------|-----------|--------------------|--------------------|--------------------|
| 2 | 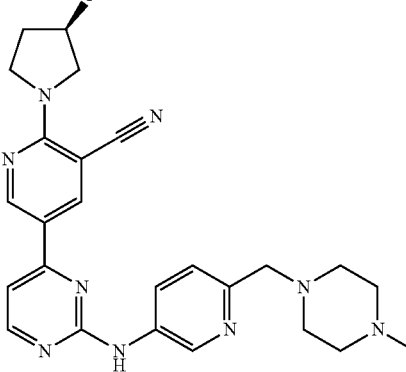 | 21 nM | 20 nM | |
| 3 | 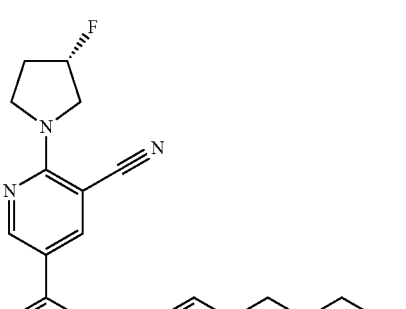 | 24 nM | 17 nM | |

Pharmacokinetic

Pharmacokinetic evaluation was performed in female Balb-C mice. For intravenous administration (IV) compounds were typically dosed at 0.5 mg/Kg in a dose volume of 5 mL/Kg via the tail vein. Compounds were typically dosed in a vehicle of 5% DMSO/95% (Kelptose 20% w/v in phosphate buffered saline (PBS) pH 7.4). Other dosing vehicles known to those skilled in the art can also be used. In order to minimise animal usage, compounds were typically dosed as cassettes containing 3 other compounds such that the total compound burden in any single experiment did not exceed 2 mg/Kg.

Blood samples were taken by cardiac puncture under terminal anaesthesia (isoflurane) at 8 time points between 1 minute and 10 hours following IV administration, typically 1 min, 5 min, 15 min, 30 min, 1 h, 3 h, 6 h and 10 h post dosing. In some instances 2 h, 4 h and 8 h were used for the final 3 time points due to greater convenience. N=3 animals were used per time point. Plasma was immediately obtained by centrifugation, and the resulting samples frozen until analysis. Samples, along with a calibration curve prepared by spiking the compounds into control plasma, were subsequently prepared for quantitative analysis by precipitation of the plasma proteins with acetonitrile. Analysis was by ultra-high performance liquid chromatography (Agilent 1290 system) coupled to time-of-flight mass spectrometry, using electrospray ionisation (Agilent 6550 system). Pharmacokinetic parameters were determined by non-compartmental analysis of mean concentration data using Phoenix WinNonlin v6.4

(i) Volume of Distribution (Vd) in Mice

The volume of distribution (Vd) is the theoretical volume into which a drug appears to be distributed assuming it is present at the same concentration everywhere as it is in plasma.

The Vd at steady state (Vdss) is calculated by multiplying the clearance (Cl) by the mean residence time (MRT). Clearance is measured by dividing the dose by the Area under the concentration time curve. Cl=Dose/$AUC_{0-\infty}$ $$Vdss = Cl \times MRT$$

The mean residence time is calculated by dividing the area under the second moment curve (AUMC) by the area under the concentration time curve (AUC). The second moment curve can be generated by plotting concentration versus concentration×time $$MRT = AUMC/AUC$$

(ii) $t_{1/2}$ in Mice (Estimated)

The compound half life ($t_{1/2}$) is the time for the concentration of the drug to halve in the plasma. The terminal half life was typically estimated from the gradient of a log concentration/time plot using the last 3 points. Both the Cl and the Vd contribute to the observed half life. A larger Vd and smaller Cl gives a longer $t_{1/2}$.

Table 2 shows the Vd and $t_{1/2}$ in mice for the exemplified compounds of the invention. The results in Table 2 show that the compounds of the present invention have excellent pharmacokinetic properties. Table 3 shows the Vd and $t_{1/2}$ in mice for certain compounds described in WO 2014/128486.

The compounds in Table 3 have structural similarities with the compounds of the present invention.

As can be seen from Tables 2 and 3, the compounds of the present invention all have a higher Vd and $t_{1/2}$ in mice compared Comparative Examples 1, 2, 4 and 5. A higher Vd indicates that a compound has a greater amount of tissue distribution. A long half-life ($t_{1/2}$) of a compound is favourable because it results in the need for the compound to be administered less frequently. As such, the compounds of the present invention have more favourable pharmacokinetic properties than the Comparative Examples.

TABLE 2

| Ex. No. | Structure | Vd (L/Kg) | t½ (h) |
|---|---|---|---|
| 1 | 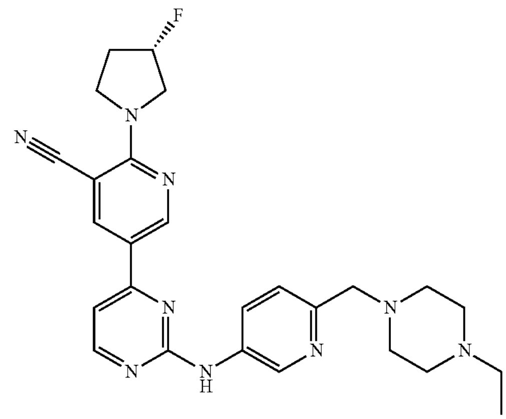 [SMILES: CCN1CCN(Cc2ccc(Nc3nccc(-c4cnc(N5CC[C@H](F)C5)c(C#N)c4)n3)cn2)CC1] | 3.3 | 1.7 |
| 2 | 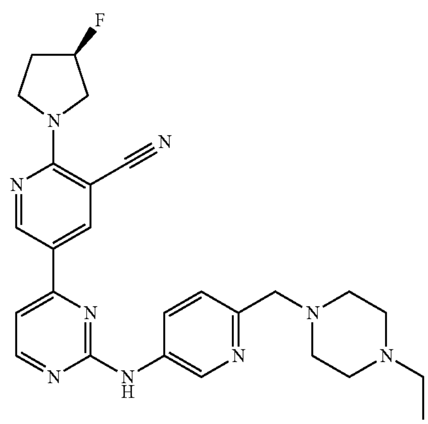 [SMILES: CCN1CCN(Cc2ccc(Nc3nccc(-c4cnc(N5CC[C@@H](F)C5)c(C#N)c4)n3)cn2)CC1] | 5.6 | 2.2 |
| 3 | 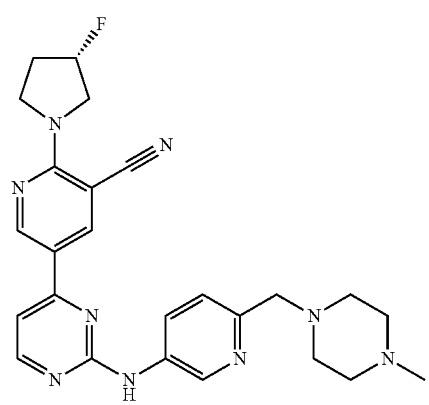 [SMILES: CN1CCN(Cc2ccc(Nc3nccc(-c4cnc(N5CC[C@H](F)C5)c(C#N)c4)n3)cn2)CC1] | 4.6 | 2.4 |

TABLE 3
| Comparative Example No. (Compound No. from WO 2014/128486) | Structure | Vd (L/Kg) | t½ (h) |
|---|---|---|---|
| Comp. Ex. 1 (DMX-68) | 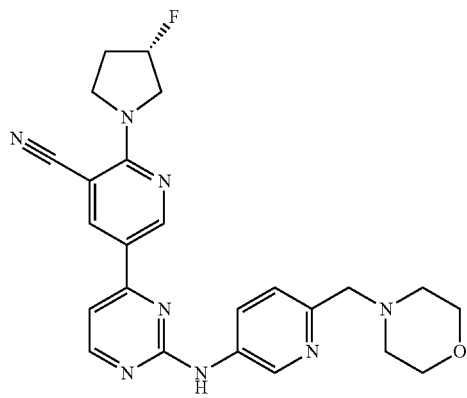 | 0.3 | 0.5 |
| Comp. Ex. 2 (DMX-102) | 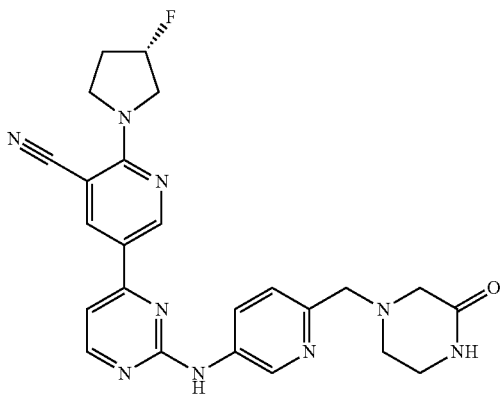 [SMILES: N#Cc1cc(-c2ccnc(Nc3ccc(CN4CCNC(=O)C4)nc3)n2)cnc1N1CC[C@H](F)C1] | 0.74 | 0.68 |

TABLE 3-continued

| Comparative Example No. (Compound No. from WO 2014/128486) | Structure | Vd (L/Kg) | t½ (h) |
|---|---|---|---|
| Comp. Ex. 4 (DMX-17) | [structure] | 0.54 | 0.5 |
| Comp. Ex. 5 (DMX-34) | [structure] | 0.7 | 0.7 |

Metabolic Stability

Human Hepatocyte (Liver Cell) Stability

Commercially available cryopreserved pooled human hepatocytes were purchased and stored in liquid nitrogen prior to use. Williams E media supplemented with 2 mM L-glutamine and 25 mM HEPES and the appropriate test compound (final substrate concentration 3 µM; final DMSO concentration 0.25%) were pre-incubated at 37° C. prior to the addition of a suspension of cryopreserved human hepatocytes (final cell density $0.5\times10^6$ viable cells/mL in Williams E media supplemented with 2 mM L-glutamine and 25 mM HEPES) to initiate the reaction. The final incubation volume is 500 µL. Two control compounds were included in each test alongside the vehicle control, typically verapamil and umbelliferone.

The reactions were stopped after 0 min, 5 min, 20 min, 40 min and 60 min by transferring 50 µL of the incubate to 100 µL methanol containing an internal standard. The termination plates were subsequently centrifuged at 2500 rpm at 4° C. to precipitate the protein. Following protein precipitation the sample supernatants are combined in cassettes of up to 4 compounds and analysed by LC-MS/MS conditions.

The In peak area ratio (compound peak area/internal standard peak area) was plotted against time and the gradient of the line determined.

Elimination rate constant $(k)=-$(gradient)

Half life$(t_{1/2})$(min)$=0.693/k$ $V$(µL/$10^6$ cells)=Incubation volume (µL)/number of cells in incubation ($\times 10^6$)

Intrinsic Clearance$(Cl_{int})$(µL/min/million cells)$=V\times 0.693/t_{1/2}$

If the two control compounds are not within historical specified limits then the results are rejected and the experiment repeated.

The human hepatocyte (liver cell) stability results for the exemplified compounds of the invention are shown in Table 4, below. The compounds of the present invention have good metabolic stability. The human hepatocyte (liver cell) stability of certain compounds described in WO 2014/128486 are included in Table 5 as Comparative Examples. The compounds chosen as Comparative Examples are compounds exemplified in WO 2014/128486 that have structural similarities with the compounds of the present invention. It can be seen from Tables 4 and 5 that the compounds of the present invention have comparable or better metabolic stability than Comparative Examples 1 to 5 disclosed in WO 2014/128486.

TABLE 4

| Ex. No. | Structure | Human hepatocyte stability (μL/min/10⁶ cells) |
|---|---|---|
| 1 | 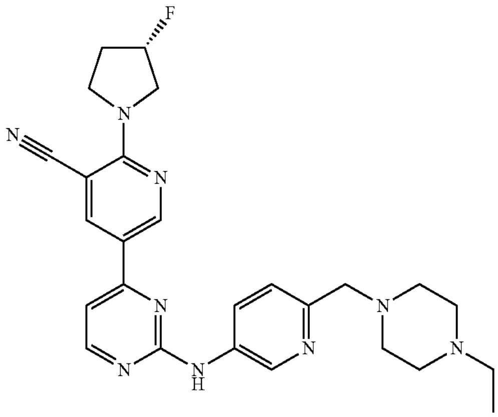 [SMILES: CCN1CCN(Cc2ccc(Nc3nccc(-c4cnc(N5CC[C@H](F)C5)c(C#N)c4)n3)cn2)CC1] | 11 |
| 2 | 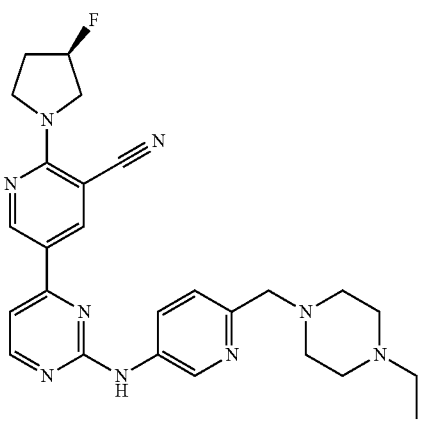 [SMILES: CCN1CCN(Cc2ccc(Nc3nccc(-c4cnc(N5CC[C@@H](F)C5)c(C#N)c4)n3)cn2)CC1] | 8 |
| 3 | 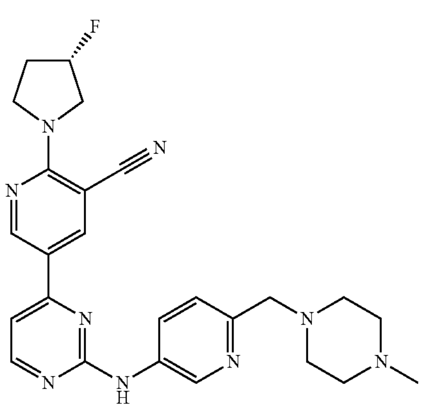 [SMILES: CN1CCN(Cc2ccc(Nc3nccc(-c4cnc(N5CC[C@H](F)C5)c(C#N)c4)n3)cn2)CC1] | 7 |

TABLE 5

| Comparative Example No. (Compound No. from WO 2014/128486) | Structure | Human Heps (μL/min/10⁶ cells) |
|---|---|---|
| Comp. Ex. 1 (DMX-68) | 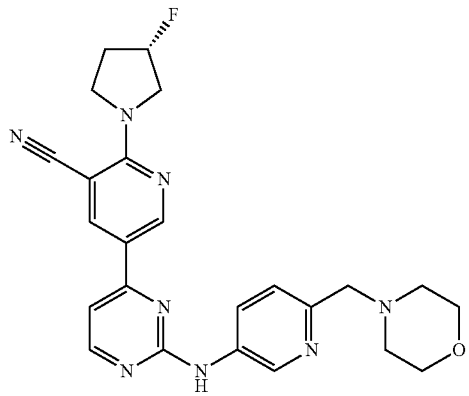 [SMILES: N#Cc1cc(-c2ccnc(Nc3ccc(CN4CCOCC4)nc3)n2)cnc1N1CC[C@H](F)C1] | 13 |
| Comp. Ex. 2 (DMX-102) | 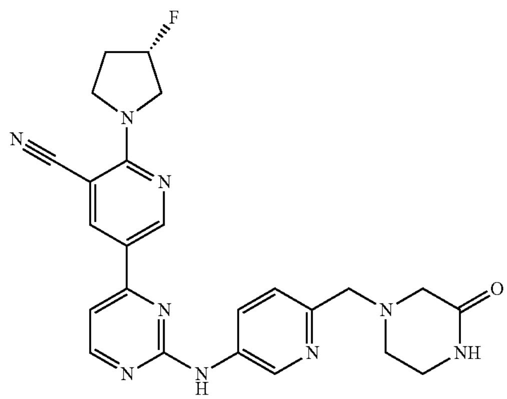 [SMILES: N#Cc1cc(-c2ccnc(Nc3ccc(CN4CCNC(=O)C4)nc3)n2)cnc1N1CC[C@H](F)C1] | ≤6 |
| Comp. Ex. 3 (DMX-24) | 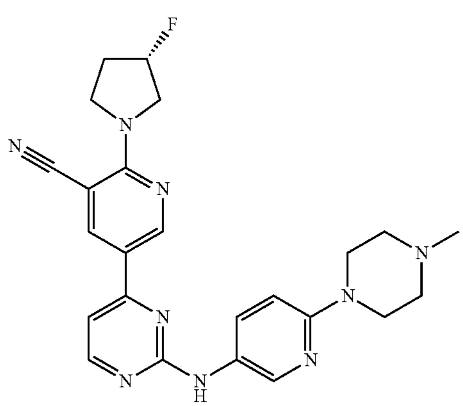 [SMILES: CN1CCN(c2ccc(Nc3nccc(-c4cnc(N5CC[C@H](F)C5)c(C#N)c4)n3)cn2)CC1] | 48 |

TABLE 5-continued

| Comparative Example No. (Compound No. from WO 2014/128486) | Structure | Human Heps (μL/min/10⁶ cells) |
|---|---|---|
| Comp. Ex. 4 (DMX-17) | 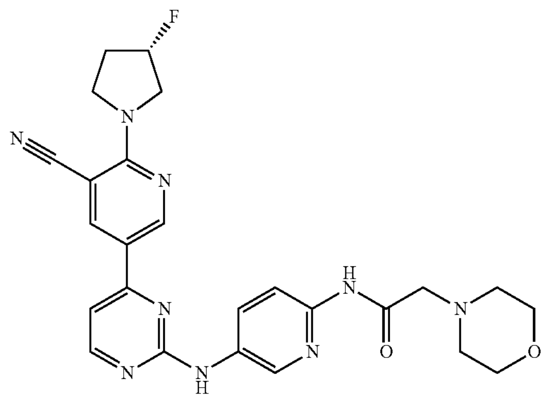 [SMILES: N#Cc1cc(-c2ccnc(Nc3ccc(NC(=O)CN4CCOCC4)nc3)n2)cnc1N1CC[C@H](F)C1] | 6 |
| Comp. Ex. 5 (DMX-34) | 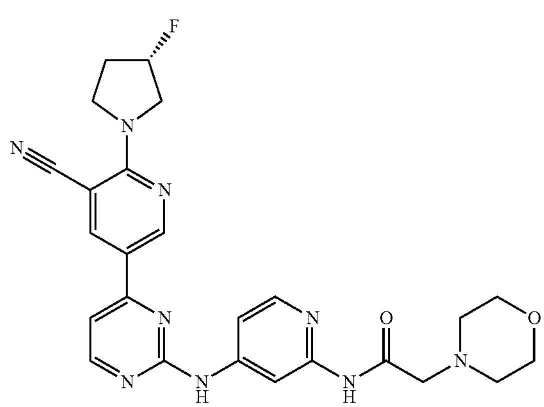 [SMILES: N#Cc1cc(-c2ccnc(Nc3ccnc(NC(=O)CN4CCOCC4)c3)n2)cnc1N1CC[C@H](F)C1] | 6 |

In summary, the biological testing of the compounds reported herein shows that the compounds of the present invention have comparable potency against the target enzymes IKKε and TBK1, and comparable human hepatocyte metabolic stability compared to the Comparative Examples exemplified in WO 2014/128486. Very surprisingly, pharmacokinetic testing of the compounds has shown that the compounds of the present invention have superior pharmacokinetics based upon the Vd (Volume of Distribution) and measured $t_{1/2}$ (half-life) than the Comparative Examples exemplified in WO 2014/128486.

The invention claimed is:

1. A compound of formula (I), or a pharmaceutically acceptable salt thereof,

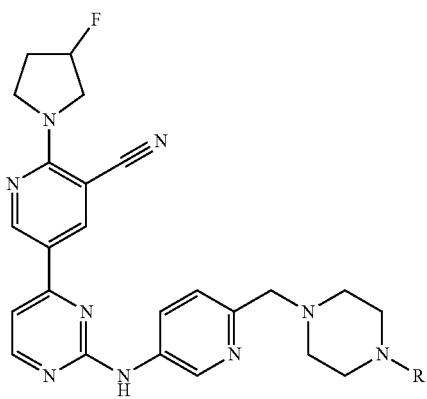

(I)

wherein R is —CH₃ or —CH₂CH₃.

2. The compound of claim 1 or a pharmaceutically acceptable salt thereof, wherein the compound is a compound of formula (Ia):

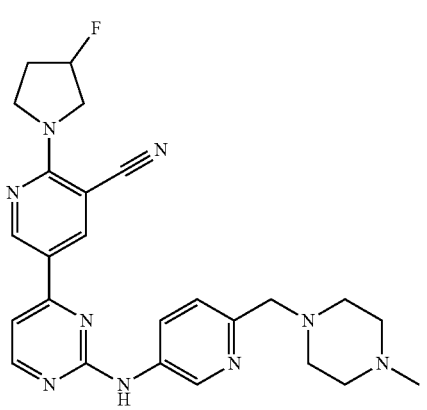

(Ia)

3. The compound of claim 1 or a pharmaceutically acceptable salt thereof, wherein the compound is a compound of formula (Ib):

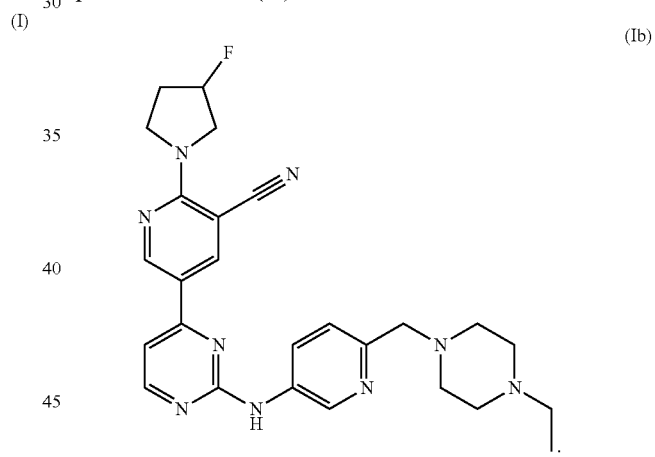

(Ib)

4. The compound of claim 1 or a pharmaceutically acceptable salt thereof, wherein the compound is

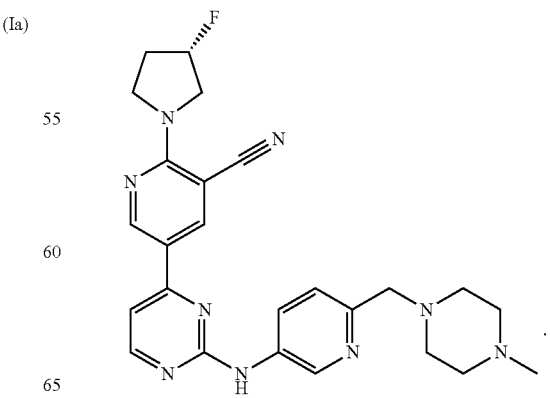

5. The compound of claim 1 or a pharmaceutically acceptable salt thereof, wherein the compound is

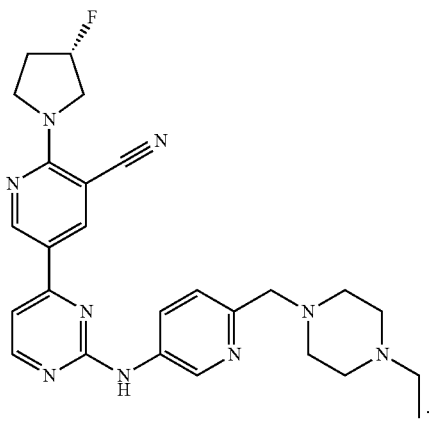 [SMILES: CCN1CCN(Cc2ccc(Nc3nccc(-c4cnc(N5CC[C@H](F)C5)c(C#N)c4)n3)cn2)CC1]

6. The compound of claim 1 or a pharmaceutically acceptable salt thereof, wherein the compound is

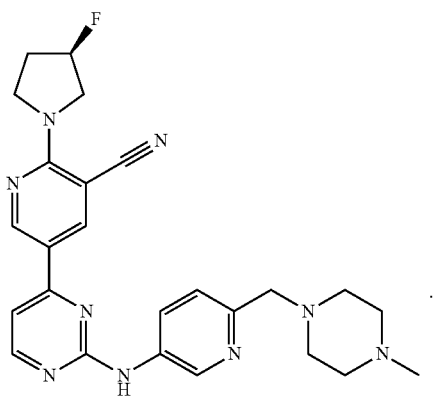 [SMILES: CN1CCN(Cc2ccc(Nc3nccc(-c4cnc(N5CC[C@@H](F)C5)c(C#N)c4)n3)cn2)CC1]

7. The compound of claim 1 or a pharmaceutically acceptable salt thereof, wherein the compound is

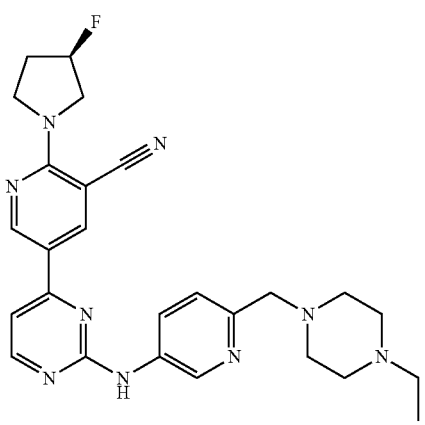

8. A pharmaceutical composition comprising the compound of claim 1 or a pharmaceutically acceptable salt thereof, and a pharmaceutically suitable carrier.

9. The pharmaceutical composition of claim 8, further comprising an additional active agent.

10. A method of treating a disease or disorder mediated by IKKε, TBK1 and/or SIK2 mechanisms in a subject, which comprises administering the compound of claim 1 or a pharmaceutically acceptable salt thereof to the subject.

11. The method of claim 10, wherein the disease or disorder is mediated by IKKε and/or TBK1.

12. The method of claim 10, wherein the disease or disorder is an inflammatory or tissue repair disorder, an autoimmune disease, osteoarthritis, osteoporosis, a fibrotic disease, dermatosis, tissue or organ rejection, Alzheimer's disease, stroke, atherosclerosis, restenosis, obesity, diabetes, glomerulonephritis, cancer, cachexia, adult respiratory distress syndrome, Ataxia Telangiestasia or primary open-angle glaucoma.

13. The method of claim 12, wherein the disease or disorder is inflammation associated with infection, giant cell arteritis, rheumatoid arthritis, inflammatory bowel disease, asthma, chronic obstructive pulmonary disease (COPD), lupus, multiple sclerosis, psoriatic arthritis, ankylosing spondylitis, Aicardi-Goutiéres Syndrome, Sjögren's Syndrome, acquired immune deficiency syndrome (AIDS), septic shock, psoriasis, atopic dermatitis, ultraviolet radiation (UV)-induced skin damage, or Hodgkin's disease.

14. The method of claim 13, wherein the disease or disorder is systemic lupus erythematosus, lupus nephritis, familial chilblain lupus, cutaneous lupus or inflammations associated with viral infection.

15. The method of claim 12, wherein the disease or disorder is an inflammatory or tissue repair disorder, or an autoimmune disease.

16. The method of claim 15, wherein the disease or disorder is rheumatoid arthritis or lupus.

17. The method of claim 12 wherein the inflammatory disorder is an aberrant inflammatory response.

18. The method of claim 10, wherein the disease or disorder is associated with increased Interferon Signature Genes (ISGs) profiles.

19. The method of claim 18, wherein the disease or disorder is an autoimmune disease with increased ISGs profiles.

20. The method of claim 10, wherein the disease or disorder is cancer.

21. The method of claim 20, wherein the cancer is a cancer in which tumour growth and/or survival is dependent upon IKKε kinase activity, a cancer harbouring a Ras mutation, a cancer involving amplification of the 1q32 gene locus or.

22. The method of claim 20 wherein the cancer is breast cancer, ovarian cancer, lung cancer, prostate cancer, myeloma, leukemia, oral cancer, pancreatic cancer, bowel cancer or skin cancer.

23. The method of claim 21 wherein the cancer harbouring a Ras mutation is a cancer which harbours a K-Ras mutation.

24. The method of claim 21 wherein the cancer which is Ras dependent is a Ras dependent tumour or a K-Ras dependent tumour.

* * * * *